(12) United States Patent
Taylor et al.

(10) Patent No.: US 10,350,440 B2
(45) Date of Patent: Jul. 16, 2019

(54) ULTRASOUND-BASED NEUROMODULATION SYSTEM

(71) Applicant: ReCor Medical, Inc., Palo Alto, CA (US)

(72) Inventors: Kevin Taylor, San Mateo, CA (US); Jaime Merino, Elmont, NY (US); Paul E. Chandler, Santa Cruz, CA (US); Jacob Raquet, Los Gatos, CA (US)

(73) Assignee: ReCor Medical, Inc., Palo Alto, CA (US)

( * ) Notice: Subject to any disclaimer, the term of this patent is extended or adjusted under 35 U.S.C. 154(b) by 828 days.

(21) Appl. No.: 14/209,948

(22) Filed: Mar. 13, 2014

(65) Prior Publication Data

US 2014/0277033 A1    Sep. 18, 2014

Related U.S. Application Data

(60) Provisional application No. 61/784,790, filed on Mar. 14, 2013.

(51) Int. Cl.
*A61N 7/00* (2006.01)
*A61B 18/04* (2006.01)
(Continued)

(52) U.S. Cl.
CPC ...... *A61N 7/022* (2013.01); *A61B 17/320068* (2013.01); *A61B 18/1492* (2013.01); *A61B 18/04* (2013.01); *A61B 2018/0022* (2013.01); *A61B 2018/00023* (2013.01); *A61B 2018/00285* (2013.01); *A61B 2018/00404* (2013.01); *A61B 2018/00434* (2013.01); *A61B 2018/00511* (2013.01); *A61B 2018/00577* (2013.01); *A61N 2007/003* (2013.01); *A61N 2007/0078* (2013.01)

(58) Field of Classification Search
None
See application file for complete search history.

(56) References Cited

U.S. PATENT DOCUMENTS 3,938,502 A    2/1976 Bom
4,802,490 A    2/1989 Johnston
(Continued)

FOREIGN PATENT DOCUMENTS

CN    1441651 A    9/2003
CN    1763245.5 A    4/2006
(Continued)

OTHER PUBLICATIONS

Bhatt, et al., A Controlled Trial of Renal Denervation for Resistant Hypertension, N. Engl. J. Med., 370:1393-1401 (2014).
(Continued)

*Primary Examiner* — Jaymi E Della
(74) *Attorney, Agent, or Firm* — Foley & Lardner LLP; Christopher C. Bolten; Nicola A. Pisano

(57) ABSTRACT

A neuromodulation system including a catheter having a balloon along its distal end is disclosed in several embodiments. An ultrasound transducer positioned within an interior of the balloon can be selectively activated to emit acoustic energy radially outwardly in order to target nerve tissue and other portions of the subject anatomy. In some embodiments, the system is configured to be delivered over a guidewire.

21 Claims, 6 Drawing Sheets

(51) Int. Cl.
*A61N 7/02* (2006.01)
*A61B 17/32* (2006.01)
*A61B 18/14* (2006.01)
*A61B 18/00* (2006.01)

(56) References Cited

U.S. PATENT DOCUMENTS

| | | | |
|---|---|---|---|
| 4,841,977 A * | 6/1989 | Griffith | A61B 8/12 |
| | | | 29/25.35 |
| 5,295,992 A | 3/1994 | Cameron | |
| 5,295,995 A | 3/1994 | Kleiman | |
| 5,308,356 A | 5/1994 | Blackshear et al. | |
| 5,324,255 A | 6/1994 | Passafaro et al. | |
| 5,327,885 A | 7/1994 | Griffith | |
| 5,354,200 A | 10/1994 | Klein et al. | |
| 5,354,220 A * | 10/1994 | Ganguly | A61B 5/0215 |
| | | | 439/675 |
| 5,400,267 A | 3/1995 | Denen et al. | |
| 5,423,220 A | 6/1995 | Finsterwald et al. | |
| 5,456,259 A | 10/1995 | Barlow et al. | |
| 5,524,491 A | 6/1996 | Cavalloni | |
| 5,620,479 A | 4/1997 | Diederich | |
| 5,630,837 A | 5/1997 | Crowley | |
| 5,713,849 A | 2/1998 | Bosma et al. | |
| 5,722,397 A | 3/1998 | Eppstein | |
| 5,769,812 A | 6/1998 | Stevens et al. | |
| 5,775,338 A | 7/1998 | Hastings | |
| 5,803,083 A | 9/1998 | Buck et al. | |
| 5,938,645 A | 8/1999 | Gordon | |
| 6,097,985 A | 8/2000 | Kasevich et al. | |
| 6,102,863 A | 8/2000 | Pflugrath et al. | |
| 6,117,101 A | 9/2000 | Diederich et al. | |
| 6,128,522 A | 10/2000 | Acker et al. | |
| 6,149,596 A | 11/2000 | Bancroft | |
| 6,190,377 B1 | 2/2001 | Kuzdrall | |
| 6,216,704 B1 | 4/2001 | Ingle et al. | |
| 6,277,077 B1 | 8/2001 | Brisken et al. | |
| 6,299,583 B1 | 10/2001 | Eggers et al. | |
| 6,355,030 B1 | 3/2002 | Aldrich et al. | |
| 6,475,146 B1 | 11/2002 | Frelburger et al. | |
| 6,492,762 B1 | 12/2002 | Pant et al. | |
| 6,517,534 B1 | 2/2003 | McGovern et al. | |
| 6,599,256 B1 | 7/2003 | Acker et al. | |
| 6,599,288 B2 | 7/2003 | Maguire et al. | |
| 6,607,502 B1 * | 8/2003 | Maguire | A61B 17/2202 |
| | | | 604/22 |
| 6,635,054 B2 | 10/2003 | Fjield et al. | |
| 6,645,202 B1 | 11/2003 | Pless et al. | |
| 6,669,638 B1 | 12/2003 | Miller et al. | |
| 6,712,767 B2 | 3/2004 | Hossack et al. | |
| 6,740,040 B1 | 5/2004 | Mandrusov et al. | |
| 6,763,722 B2 | 7/2004 | Fjield et al. | |
| 6,793,635 B2 | 9/2004 | Ryan et al. | |
| 6,913,581 B2 | 7/2005 | Corl et al. | |
| 6,953,469 B2 | 10/2005 | Ryan | |
| 6,978,174 B2 | 12/2005 | Gelfand et al. | |
| 7,162,303 B2 | 1/2007 | Levin et al. | |
| 7,285,116 B2 | 10/2007 | De La Rama et al. | |
| 7,291,413 B2 | 11/2007 | Allen et al. | |
| 7,297,413 B2 | 11/2007 | Mitsumori | |
| 7,347,852 B2 | 3/2008 | Hobbs et al. | |
| 7,473,224 B2 | 1/2009 | Makin | |
| 7,540,846 B2 | 6/2009 | Harhen et al. | |
| 7,573,182 B2 | 8/2009 | Savage | |
| 7,591,996 B2 | 9/2009 | Hwang et al. | |
| 7,617,005 B2 | 11/2009 | Demarais et al. | |
| 7,620,451 B2 | 11/2009 | Demarais et al. | |
| 7,625,371 B2 | 12/2009 | Morris et al. | |
| 7,647,115 B2 | 1/2010 | Levin et al. | |
| 7,653,438 B2 | 1/2010 | Deem et al. | |
| 7,678,104 B2 | 3/2010 | Keidar | |
| 7,717,948 B2 | 5/2010 | Demarais et al. | |
| 7,756,583 B2 | 7/2010 | Demarais et al. | |
| 7,837,676 B2 | 11/2010 | Sinelnikov et al. | |
| 7,846,317 B2 | 12/2010 | Meltzer et al. | |
| 7,873,417 B2 | 1/2011 | Demarais et al. | |
| 7,937,143 B2 | 5/2011 | Demarais et al. | |
| 8,131,371 B2 | 3/2012 | Demarals et al. | |
| 8,233,221 B2 | 7/2012 | Suijver et al. | |
| 8,251,986 B2 | 8/2012 | Chornenky et al. | |
| 8,287,472 B2 | 10/2012 | Ostrovsky et al. | |
| 8,475,442 B2 | 7/2013 | Hall et al. | |
| 8,485,993 B2 | 7/2013 | Orszulak et al. | |
| 8,504,147 B2 | 8/2013 | Deem et al. | |
| D697,036 S | 1/2014 | Kay et al. | |
| 8,715,209 B2 | 5/2014 | Gertner | |
| 8,734,438 B2 | 5/2014 | Behnke | |
| D708,810 S | 7/2014 | Lewis, Jr. | |
| 8,808,345 B2 | 8/2014 | Clark et al. | |
| D712,352 S | 9/2014 | George et al. | |
| D712,353 S | 9/2014 | George et al. | |
| D712,833 S | 9/2014 | George et al. | |
| 8,974,445 B2 | 3/2015 | Warnking et al. | |
| 9,675,413 B2 | 6/2017 | Deem et al. | |
| 9,700,372 B2 | 7/2017 | Schaer | |
| 9,707,034 B2 | 7/2017 | Schaer | |
| 9,943,666 B2 | 4/2018 | Warnking | |
| 9,981,108 B2 | 5/2018 | Warnking | |
| 10,039,901 B2 | 8/2018 | Warnking | |
| 2001/0007940 A1 | 7/2001 | Tu et al. | |
| 2002/0002334 A1 | 1/2002 | Okuno et al. | |
| 2002/0002371 A1 | 1/2002 | Acker et al. | |
| 2002/0062123 A1 | 5/2002 | McClurken et al. | |
| 2002/0065512 A1 | 5/2002 | Fjield et al. | |
| 2002/0087156 A1 | 7/2002 | Maguire et al. | |
| 2002/0150693 A1 | 10/2002 | Kobayashi et al. | |
| 2002/0151889 A1 | 10/2002 | Swanson et al. | |
| 2002/0156469 A1 | 10/2002 | Yon et al. | |
| 2002/0165535 A1 | 11/2002 | Lesh et al. | |
| 2002/0193781 A1 | 12/2002 | Loeb | |
| 2003/0060813 A1 | 3/2003 | Loeb et al. | |
| 2003/0125726 A1 * | 7/2003 | Maguire | A61B 18/00 |
| | | | 606/41 |
| 2003/0138571 A1 | 7/2003 | Kunishi et al. | |
| 2003/0181963 A1 | 9/2003 | Pellegrino et al. | |
| 2003/0204138 A1 | 10/2003 | Choi | |
| 2003/0216721 A1 | 11/2003 | Diederich et al. | |
| 2003/0216792 A1 | 11/2003 | Levin et al. | |
| 2003/0216794 A1 | 11/2003 | Becker et al. | |
| 2003/0225331 A1 | 12/2003 | Diederich et al. | |
| 2003/0233099 A1 | 12/2003 | Danaek et al. | |
| 2004/0044286 A1 | 3/2004 | Hossack et al. | |
| 2004/0082859 A1 | 4/2004 | Schaer | |
| 2004/0167415 A1 | 8/2004 | Gelfand et al. | |
| 2004/0230116 A1 | 11/2004 | Cowan et al. | |
| 2004/0253450 A1 | 12/2004 | Seita et al. | |
| 2005/0009218 A1 | 1/2005 | Kunihiro | |
| 2005/0035901 A1 | 2/2005 | Lyon | |
| 2005/0215990 A1 | 9/2005 | Govari | |
| 2005/0234523 A1 | 10/2005 | Levin et al. | |
| 2005/0256518 A1 | 11/2005 | Rama et al. | |
| 2005/0288730 A1 | 12/2005 | Deem et al. | |
| 2006/0041277 A1 | 2/2006 | Deem et al. | |
| 2006/0058711 A1 * | 3/2006 | Harhen | A61B 17/2202 |
| | | | 601/2 |
| 2006/0064081 A1 | 3/2006 | Rosinko | |
| 2006/0088705 A1 | 4/2006 | Mitsumori | |
| 2006/0100514 A1 | 5/2006 | Lopath | |
| 2006/0121200 A1 | 6/2006 | Halpert et al. | |
| 2006/0154072 A1 | 7/2006 | Schlossman et al. | |
| 2006/0155269 A1 | 7/2006 | Warnking | |
| 2006/0184072 A1 | 8/2006 | Manna | |
| 2006/0212076 A1 | 9/2006 | Demarais et al. | |
| 2006/0212078 A1 | 9/2006 | Demarais et al. | |
| 2006/0229594 A1 | 10/2006 | Francischelli et al. | |
| 2006/0241523 A1 | 10/2006 | Sinelnikov et al. | |
| 2006/0265014 A1 | 11/2006 | Demarais et al. | |
| 2006/0265015 A1 | 11/2006 | Demarais et al. | |
| 2006/0270976 A1 | 11/2006 | Savage et al. | |
| 2006/0276852 A1 | 12/2006 | Demarais et al. | |
| 2007/0124458 A1 | 5/2007 | Kumar | |
| 2007/0129720 A1 | 6/2007 | Demarais et al. | |
| 2007/0129760 A1 | 6/2007 | Demarais et al. | |
| 2007/0135875 A1 | 6/2007 | Demarais et al. | |

(56) References Cited

U.S. PATENT DOCUMENTS

| | | |
|---|---|---|
| 2007/0173899 A1 | 7/2007 | Levin et al. |
| 2007/0175359 A1 | 8/2007 | Hwang |
| 2007/0203547 A1 | 8/2007 | Costello et al. |
| 2007/0203549 A1 | 8/2007 | Demarais et al. |
| 2007/0249046 A1 | 10/2007 | Shields, Jr. |
| 2007/0255267 A1 | 11/2007 | Diederich et al. |
| 2007/0255342 A1 | 11/2007 | Laufer |
| 2007/0265609 A1 | 11/2007 | Thapliyal et al. |
| 2007/0265610 A1 | 11/2007 | Thapliyal et al. |
| 2007/0265687 A1 | 11/2007 | Deem et al. |
| 2007/0282407 A1 | 12/2007 | Demarais et al. |
| 2007/0293762 A1 | 12/2007 | Sawada et al. |
| 2008/0052186 A1 | 2/2008 | Walker et al. |
| 2008/0151001 A1 | 6/2008 | Sudo et al. |
| 2008/0252172 A1 | 10/2008 | Yetter et al. |
| 2008/0255449 A1 | 10/2008 | Warnking et al. |
| 2008/0255478 A1 | 10/2008 | Burdette |
| 2008/0255642 A1 | 10/2008 | Zarins et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0118125 A1 | 5/2009 | Kobayashi et al. |
| 2009/0118725 A1 | 5/2009 | Auth et al. |
| 2009/0124964 A1 | 5/2009 | Leach et al. |
| 2009/0149753 A1 | 6/2009 | Govari et al. |
| 2009/0171202 A1 | 7/2009 | Kirkpatrick et al. |
| 2009/0189485 A1 | 7/2009 | Iyoki |
| 2009/0204006 A1 | 8/2009 | Wakabayashi et al. |
| 2009/0221939 A1 | 9/2009 | Demarais et al. |
| 2009/0228003 A1 | 9/2009 | Sinelnikov |
| 2009/0248011 A1 | 10/2009 | Hlavka et al. |
| 2009/0299360 A1 | 12/2009 | Ormsby |
| 2009/0312673 A1 | 12/2009 | Thapliyal et al. |
| 2009/0312693 A1 | 12/2009 | Thapliyal et al. |
| 2009/0312755 A1 | 12/2009 | Thapliyal et al. |
| 2010/0016762 A1 | 1/2010 | Thapliyal et al. |
| 2010/0033940 A1 | 2/2010 | Yamaguchi et al. |
| 2010/0049099 A1 | 2/2010 | Thapliyal et al. |
| 2010/0113928 A1 | 5/2010 | Thapliyal et al. |
| 2010/0113985 A1 | 5/2010 | Thapliyal et al. |
| 2010/0114094 A1 | 5/2010 | Thapliyal et al. |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0137952 A1 | 6/2010 | Demarais et al. |
| 2010/0152582 A1 | 6/2010 | Thapliyal et al. |
| 2010/0168731 A1 | 7/2010 | Wu et al. |
| 2010/0168737 A1 | 7/2010 | Grunewald |
| 2010/0168739 A1 | 7/2010 | Wu et al. |
| 2010/0174282 A1 | 7/2010 | Demarais et al. |
| 2010/0179424 A1 | 7/2010 | Warnking et al. |
| 2010/0189974 A1 | 7/2010 | Ochi et al. |
| 2010/0191112 A1 | 7/2010 | Demarais et al. |
| 2010/0198065 A1 | 8/2010 | Thapliyal et al. |
| 2010/0249859 A1 | 9/2010 | Dilorenzo |
| 2010/0291722 A1 | 11/2010 | Kim |
| 2011/0004184 A1 | 1/2011 | Proksch et al. |
| 2011/0060324 A1 | 3/2011 | Wu et al. |
| 2011/0087096 A1 | 4/2011 | Behar |
| 2011/0087097 A1 | 4/2011 | Behar |
| 2011/0104060 A1 | 5/2011 | Seward |
| 2011/0112400 A1 | 5/2011 | Emery et al. |
| 2011/0118598 A1 | 5/2011 | Gertner |
| 2011/0137298 A1 | 6/2011 | Nguyen et al. |
| 2011/0172527 A1 | 7/2011 | Gertner |
| 2011/0178516 A1 | 7/2011 | Orszulak et al. |
| 2011/0200171 A1 | 8/2011 | Beetel et al. |
| 2011/0208096 A1 | 8/2011 | Demarais et al. |
| 2011/0257523 A1 | 10/2011 | Hastings et al. |
| 2011/0257562 A1 | 10/2011 | Schaer |
| 2011/0257563 A1 | 10/2011 | Thapliyal et al. |
| 2011/0257564 A1 | 10/2011 | Demarais et al. |
| 2011/0301662 A1 | 12/2011 | Bar-Yoseph et al. |
| 2011/0319765 A1 | 12/2011 | Gertner et al. |
| 2012/0004656 A1 | 1/2012 | Jackson et al. |
| 2012/0065493 A1 | 3/2012 | Gertner |
| 2012/0065554 A1 | 3/2012 | Pikus |
| 2012/0078278 A1 | 3/2012 | Bales et al. |
| 2012/0095461 A1 | 4/2012 | Herscher et al. |
| 2012/0123243 A1 | 5/2012 | Hastings |
| 2012/0123303 A1 | 5/2012 | Sogard et al. |
| 2012/0143097 A1 | 6/2012 | Pike, Jr. |
| 2012/0165667 A1 | 6/2012 | Altmann et al. |
| 2012/0172723 A1 | 7/2012 | Gertner |
| 2012/0215106 A1 | 8/2012 | Sverdlik et al. |
| 2012/0232436 A1 | 9/2012 | Warnking |
| 2012/0238918 A1 | 9/2012 | Gertner |
| 2012/0238919 A1 | 9/2012 | Gertner |
| 2012/0265198 A1 | 10/2012 | Crow et al. |
| 2012/0316439 A1 | 12/2012 | Behar |
| 2013/0012844 A1 | 1/2013 | Demarais et al. |
| 2013/0072928 A1 | 3/2013 | Schaer |
| 2013/0090650 A1 | 4/2013 | Jenson et al. |
| 2013/0103064 A1 | 4/2013 | Arenson et al. |
| 2013/0110012 A1 | 5/2013 | Gertner |
| 2013/0131668 A1 | 5/2013 | Schaer |
| 2013/0138018 A1 | 5/2013 | Gertner |
| 2013/0158441 A1 | 6/2013 | Demarais et al. |
| 2013/0158442 A1 | 6/2013 | Demarais et al. |
| 2013/0165822 A1 | 6/2013 | Demarais et al. |
| 2013/0165924 A1 | 6/2013 | Mathur et al. |
| 2013/0197555 A1 | 8/2013 | Schaer |
| 2013/0204167 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0274658 A1 | 10/2013 | Steinke et al. |
| 2013/0282084 A1 | 10/2013 | Mathur et al. |
| 2013/0304047 A1 | 11/2013 | Grunewald et al. |
| 2013/0331739 A1 | 12/2013 | Gertner |
| 2014/0012133 A1 | 1/2014 | Sverdlik et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039477 A1 | 2/2014 | Sverdlik et al. |
| 2014/0046313 A1 | 2/2014 | Pederson et al. |
| 2014/0067029 A1 | 3/2014 | Schauer et al. |
| 2014/0074083 A1 | 3/2014 | Horn et al. |
| 2014/0107639 A1 | 4/2014 | Zhang et al. |
| 2014/0163540 A1 | 6/2014 | Iyer et al. |
| 2014/0180196 A1 | 6/2014 | Stone et al. |
| 2014/0180197 A1 | 6/2014 | Sverdlik et al. |
| 2014/0194785 A1 | 7/2014 | Gertner |
| 2014/0200489 A1 | 7/2014 | Behar et al. |
| 2014/0214018 A1 | 7/2014 | Behar et al. |
| 2014/0249524 A1 | 9/2014 | Kocur |
| 2014/0272110 A1 | 9/2014 | Taylor et al. |
| 2014/0275924 A1 | 9/2014 | Min et al. |
| 2014/0276742 A1 | 9/2014 | Nabutovsky et al. |
| 2014/0276752 A1 | 9/2014 | Wang et al. |
| 2014/0276755 A1 | 9/2014 | Cao et al. |
| 2014/0276789 A1 | 9/2014 | Dandler et al. |
| 2014/0277033 A1 | 9/2014 | Taylor et al. |
| 2015/0223877 A1 | 8/2015 | Behar et al. |
| 2015/0290427 A1 | 10/2015 | Warnking |
| 2015/0335919 A1 | 11/2015 | Behar et al. |
| 2016/0016016 A1 | 1/2016 | Taylor et al. |

FOREIGN PATENT DOCUMENTS

| | | |
|---|---|---|
| DE | 20 2005 022 060 U1 | 11/2012 |
| EP | 0 623 360 B1 | 11/1994 |
| EP | 0 659 387 A2 | 6/1995 |
| EP | 0 767 630 B1 | 4/1997 |
| EP | 0 774 276 A2 | 5/1997 |
| EP | 0 838 980 A2 | 4/1998 |
| EP | 1 042 990 A1 | 10/2000 |
| EP | 1 100 375 B1 | 5/2001 |
| EP | 1 384 445 A1 | 1/2004 |
| EP | 1 598 024 A2 | 11/2005 |
| EP | 1 647 305 B1 | 4/2006 |
| EP | 2 218 479 A2 | 8/2010 |
| EP | 2 359 764 A1 | 8/2011 |

(56) References Cited

FOREIGN PATENT DOCUMENTS

| | | |
|---|---|---|
| EP | 2 457 614 A1 | 5/2012 |
| EP | 2 460 486 B1 | 6/2012 |
| EP | 2 495 012 A1 | 9/2012 |
| EP | 2 521 593 B1 | 11/2012 |
| EP | 2 561 903 A1 | 2/2013 |
| EP | 2 561 905 A1 | 2/2013 |
| EP | 2 626 022 A2 | 8/2013 |
| EP | 2 632 373 | 9/2013 |
| EP | 2 662 041 A2 | 11/2013 |
| EP | 2 662 043 A2 | 11/2013 |
| GB | 2 037 166 A | 7/1980 |
| JP | 05-068684 A | 3/1993 |
| JP | 07-178173 A | 7/1995 |
| JP | 40-826437 A | 10/1996 |
| JP | 10-127678 A | 5/1998 |
| JP | H-10-507229 A | 7/1998 |
| JP | 11-218100 A | 8/1999 |
| JP | 2000-054153 A | 2/2000 |
| JP | 2001-111126 A | 4/2001 |
| JP | 2002-078809 A | 3/2002 |
| JP | 2003-533265 A | 11/2003 |
| JP | 2004-503324 A | 2/2004 |
| JP | 2004-130096 A | 4/2004 |
| JP | 2005-526579 A | 9/2005 |
| JP | 2005-270662 A | 10/2005 |
| JP | 2006-161116 A | 6/2006 |
| JP | 2008-513056 | 5/2008 |
| JP | 2008-515544 A1 | 5/2008 |
| JP | 2008-214669 A | 9/2008 |
| JP | 2010-503466 A1 | 2/2010 |
| JP | 2010-221038 A | 10/2010 |
| JP | 2011-219828 A | 11/2011 |
| WO | WO-90/00420 A1 | 1/1990 |
| WO | WO-92/07622 A1 | 5/1992 |
| WO | WO-92/20291 A1 | 11/1992 |
| WO | WO-94/05365 A1 | 3/1994 |
| WO | WO-94/11057 | 5/1994 |
| WO | WO-95/19143 A1 | 7/1995 |
| WO | WO-95/25472 A1 | 9/1995 |
| WO | WO-96/00039 A1 | 1/1996 |
| WO | WO-97/13463 A1 | 4/1997 |
| WO | WO-97/36548 A1 | 10/1997 |
| WO | WO-98/41178 A1 | 9/1998 |
| WO | WO-98/42403 A1 | 10/1998 |
| WO | WO-98/49957 A1 | 11/1998 |
| WO | WO-98/52465 A1 | 11/1998 |
| WO | WO-99/02096 A1 | 1/1999 |
| WO | WO-99/35987 A1 | 7/1999 |
| WO | WO-99/44519 A2 | 9/1999 |
| WO | WO-99/44523 A1 | 9/1999 |
| WO | WO-99/52423 A1 | 10/1999 |
| WO | WO-99/56812 A2 | 11/1999 |
| WO | WO-00/16850 A1 | 3/2000 |
| WO | WO-00/27292 A1 | 5/2000 |
| WO | WO-00/41881 A2 | 7/2000 |
| WO | WO-00/42934 A1 | 7/2000 |
| WO | WO-00/51511 A1 | 9/2000 |
| WO | WO-00/51683 A1 | 9/2000 |
| WO | WO-00/56237 A2 | 9/2000 |
| WO | WO-00/57495 A1 | 9/2000 |
| WO | WO-00/67648 A1 | 11/2000 |
| WO | WO-00/67656 A1 | 11/2000 |
| WO | WO-00/67659 A1 | 11/2000 |
| WO | WO-00/67830 A1 | 11/2000 |
| WO | WO-00/67832 A2 | 11/2000 |
| WO | WO-01/13357 A1 | 2/2001 |
| WO | WO-01/22897 A1 | 4/2001 |
| WO | WO-01/37925 A2 | 5/2001 |
| WO | WO-01/70114 A1 | 9/2001 |
| WO | WO-01/80723 A2 | 11/2001 |
| WO | WO-01/82814 A2 | 11/2001 |
| WO | WO-02/05868 A2 | 1/2002 |
| WO | WO-02/083196 A2 | 10/2002 |
| WO | WO-02/085192 A2 | 10/2002 |
| WO | WO-03/003930 A1 | 1/2003 |
| WO | WO-03/059437 A2 | 7/2003 |
| WO | WO-03/099382 A1 | 12/2003 |
| WO | WO-2004/023978 | 3/2004 |
| WO | WO-2004/091255 A1 | 10/2004 |
| WO | WO-2005/009218 A2 | 2/2005 |
| WO | WO-2006/041847 A1 | 4/2006 |
| WO | WO-2006/041881 A2 | 4/2006 |
| WO | WO-2006/060053 A2 | 6/2006 |
| WO | WO-2007/124458 A2 | 11/2007 |
| WO | WO-2007/135875 A1 | 11/2007 |
| WO | WO-2007/146834 A2 | 12/2007 |
| WO | WO-2008/003058 A2 | 1/2008 |
| WO | WO-2008/036479 A2 | 3/2008 |
| WO | WO-2008/052186 A2 | 5/2008 |
| WO | WO-2008/061152 A2 | 5/2008 |
| WO | WO-2008/151001 A2 | 12/2008 |
| WO | WO-2009/149315 A2 | 12/2009 |
| WO | WO-2010/033940 A1 | 3/2010 |
| WO | WO-2010/067360 A2 | 6/2010 |
| WO | WO-2011/046880 A2 | 4/2011 |
| WO | WO-2011/053757 A1 | 5/2011 |
| WO | WO-2011/082279 A2 | 7/2011 |
| WO | WO-2011/088399 A1 | 7/2011 |
| WO | WO-2011/094367 A1 | 8/2011 |
| WO | WO-2011/139589 A2 | 11/2011 |
| WO | WO-2012/112165 A1 | 8/2012 |

OTHER PUBLICATIONS

Bunch, Jared, et al., Mechanisms of Phrenic Nerve Injury During Radiofrequency Ablation at the Pulmonary Vein Orifice, Journal of Cardiovascular Electrophysiology, 16(12):1318-1325 (2005).
Campese, et al., Renal afferent denervation prevents hypertension in rats with chronic renal failure, Hypertension, 25:878-882 (1995).
Dibona, Renal nerves in compensatory renal response to contralateral renal denervation, Renal Physiology, 238 (1):F26-F30 (1980).
International Search Report & Written Opinion dated Jul. 9, 2014 in Int'l PCT Patent Application Serial No. PCT/US2014/22804.
International Search Report & Written Opinion dated Nov. 29, 2011 in International PCT Patent Appl No. PCT/US2011/025543.
International Search Report dated Feb. 9, 2014 in Int'l PCT Patent Application Serial No. PCT/US2014/022796.
Medtronic Press Release, Medtronic Announces U.S. Renal Denervation Pivotal Trial Fails to Meet Primary Efficacy Endpoint While Meeting Primary Safety Endpoint, Jan. 9, 2014.
Oliveira, et a., Renal Denervation Normalizes Pressure and Baroreceptor Reflex in High Renin Hypertension in Conscious Rats, Hypertension 19:17-21 (1992).
OnlineMathLearning.com, Volume Formula, "Volume of a Hollow Cylinder", Oct. 24, 2008.
Smithwick, R.H., Surgery in hypertension, Lancet, 2:65 (1948).
Smithwick, R.H., Surgical treatment of hypertension, Am J Med 4:744-759 (1948).
Wang, S., et al., Effects of Low Intensity Ultrasound on the Conduction Property of Neural Tissues, IEEE International Ultrasonics, Ferroelectrics, and Frequency Control, Joint 50th Anniversary Conference, 2004.
International Search Report & Written Opinion dated Jul. 9, 2014 in related Int'l PCT Patent Application Serial No. PCT/US2014/22804.
Extended EP Search Report dated Dec. 5, 2016 in EP Patent Application Serial No. 16183988.1.
www.dictionary.com/browse/degrease, retrieved Jun. 7, 2016.
Arruda, M.S., et al. "Development and validation of an ECG algorithm for identifying accessory pathway ablation site in Wolff-Parkinson-White syndrome." J Cardiovasc Electrophysiol, 9:2-12 (1998).
Avitall, B., et al. "The creation of linear continuous lesions in the atria with an expandable loop catheter." J Am Coll Cardiol, 33,4:972-974 (1999).
Bartlett, T.G., et al. "Current management of the Wolff-Parkinson-White syndrome." J Card Surg. 8:503-515 (1993).
Benito, F., et al. "Radio frequency catheter ablation of accessory pathways in infants," Heart, 78:160-162 (1997).

(56) References Cited

OTHER PUBLICATIONS

Blumenfeld, J.D., et al. "β-Adrenergic receptor blockade as a therapeutic approach for suppressing the renin-angiotensin-aldosterone system in norrnotensive and hypertensive subjects." AJH, 12:451-459 (1999).

Callans, D. J. "Narrowing of the superior vena cava—right atrium junction during radiofrequency catheter ablation for inappropriate sinus tachycardia: Analysis with intracardiac echocardiography." JACC, 33:1667-1670 (1999).

Cao, H., et al. "Flow effect on lesion formation in RF cardiac catheter ablation." IEEE T Bio-Med Eng, 48:425-433 (2001).

Chen, S.-A., et al. "Complications of diagnostic electrophysiologic studies and radiofrequency catheter ablation in patients with tachyarrhythmias: An eight-year survey of 3,966 consecutive procedures in a tertiary referral center." Am J Cardiol, 77:41-46 (1996).

Chen, Shih-Ann, M.D., "Initiation of Atrial Fibrillation by Ectopic Beats Originating From the Pulmonary Veins," Circulation 100(18):1879-86, 1999.

Chinitz, et al., "Mapping Reentry Around Atriotomy Scars Using Double Potentials," Pacing and Clinical Electrophysiology, Cardiostim 96 Proceedings, Part II, vol. 19:1978-1983 (1996).

Cioni, R., et al. "Renal artery stenting in patients with a solitary functioning kidney." Cardiovasc Intervent Radiol, 24:372-377 (2001).

Cosby, R.L., et al. "The role of the sympathetic nervous system and vasopressin in the pathogenesis of the abnormal sodium and water." Nefrologia, V, 4:271-277 (1985).

Cosio, Francisco G., "Atrial Flutter Mapping and Ablation II," Pacing & Clin. Electrophysiol. 19(6):965-75, 1996.

Cox, J.L. "The status of surgery for cardiac arrhythmias." Circulation, 71 :413-417 (1985).

Cox, J.L. et al. "Five-year experience with the Maze procedure for atrial fibrillation." Ann Thorac Surg, 56:814-824 (1993).

Cruickshank, J.M. "Beta-blockers continue to surprise us." Eur Heart J, 21:354-364 (2000).

Curtis, J.J., et al. "Surgical therapy for persistent hypertension after renal transplantation," Transplantation, 31:125-128 (1981).

Demazumder, D., et al. "Comparison of irrigated electrode designs for radiofrequency ablation of myocardium." J Intery Card Electr, 5:391-400 (2001).

DiBona, G.F. "Neural control of the kidney: Functionally specific renal sympathetic nerve fibers." Am J Physiol Regulatory Integrative Comp Physiol, 279:R1517-R1524 (2000).

DiBona, G.F. "Sympathetic nervous system and kidney in hypertension," Nephrol and Hypertension, 11:197-200 (2002).

DiBona, G.F., et al. "Neural control of renal function," Physiol Rev, 77:75-197 (1997).

DiBona, G.F., et al. "Renal hemodynamic effects of activation of specific renal sympathetic nerve fiber groups." Am J Physiol Regul Integr Comp Physiol, 276:R539-R539 (1999).

Diederich C.J. et al. "Transurethral Ultrasound Array for Prostate Thermal Therapy: Initial Studies", IEEE Transactions on Ultrasonic, Ferroelectronics and Frequency Control IEEEE USA, vol. 43, No. 6 Nov. 1996, pp. 1011-1022.

Doggrell, S.A., et al. "Rat models of hypertension, cardiac hypertrophy and failure." Cardiovasc Res, 39:89-105 (1998).

Dong Q., et al. "Diagnosis of renal vascular disease with MR angiography." RadioGraphies, 19:1535-1554 (1999).

Dubuc, M., et al. "Feasibility of cardiac cryoablation using a transvenous steerable electrode catheter," J Intery Cardiac Electrophysiol, 2:285-292 (1998).

Feld, Gregory K., "Radiofrequency Catheter Ablation for the Treatment of Human Type I Atrial Flutter," Circulation, 86(3):1233-1240 (1992).

Gallagher, John J., "Wolff-Parkinson-White Syndrome: Surgery to Radiofrequency Catheter Ablation," 1997.

Gilard, M., et al. "Angiographic anatomy of the coronary sinus and its tributaries." PACE, 21:2280-2284 (1998).

Gorisch, W., et al. "Heat-induced contraction of blood vessels." Lasers Surg Med, 2:1-13 (1982).

Haines, D.E. et al. "Tissue heating during radiofrequency catheter ablation; A thermodynamic model and observations in isolated perfused and superfused canine right ventricular free wall." PACE, 12:962-976 (1989).

Haissaguerre, et al., "Radiofrequency Catheter Ablation in Unusual Mechanisms of Atrial Fibrillation," Journal of Cardiovascular Electrophysiology, 5(9):743-1751 (1994).

Haissaguerre, et al., "Right and Left Atrial Radiofrequency Catheter Therapy of Paroxysmal Atrial Fibrillation," Journal of Cardiovascular Electrophysiology, 7(12):1133-1144 (1996).

Haissaguerre, Michel, "Electrophysiological End Point for Catheter Ablation of Atrial Fibrillation Initiated From Multiple Venous Foci," Circulation, 101:1409-1417 (2000).

Haissaguerre, Michel, M.D., "Predominant Origin of Atrial Panarrhythmic Triggers in the Pulmonary Veins: A Distinct Electrophysiologic Entity," 1997.

Haissaguerre, Michel, M.D., et al., "Spontaneous Initiation of Atrial Fibrillation by Ectopic Beats Originating in the Pulmonary Veins," The New England Journal of Medicine, 339(10):659-666 (1998).

Han, Y-M., et al. "Renal artery embolization with diluted hot contrast medium: An experimental study," J Vasc Interv Radiol, 12:862-868 (2001).

Hansen, J.M., et al. "The transplanted human kidney does not achieve functional reinnervation." Clin Sci, 87, 1:13-20 (1994).

Hatala, Robert, "Radiofrequency Catheter Ablation of Left Atrial Tachycardia Originating Within the Pulmonary Vein in a Patient with Dextrocardia," Pacing and Clinical Electrophysiology, 19(6):999-1002 (1996).

Hindricks, G. "The Multicentre European Radiofrequency Survey (MERFS): Complications of radiofrequency catheter ablation of arrhythmias." Eur Heart J, 14:1644-1653 (1993).

Ho, S.Y., et al. "Architecture of the pulmonary veins: Relevance to the radiofrequency ablation." Heart 86:265-270 (2001).

Hocini, et al., "Concealed Left Pulmonary Vein Potentials Unmasked by Left Atrial Stimulation," Pacing and Clinical Electrophysiology, 23(11):1828-1831, part 2 (2000).

Hocini, et al., "Multiple Sources initiating Atrial Fibrillation from a Single Pulmonary Vein Identified by a Circumferential Catheter," Pacing and Clinical Electrophysiology, 23(11):1828-1831, Part 2 (2000).

Hsieh, et al., "Double Multielectrode Mapping Catheters Facilitate Radiofrequency Catheter Ablation of Focal Atrial Fibrillation Originating from Pulmonary Veins," Journal of Cardiovascular Electrophysiology, 10(2):136-144 (1999).

Huang et al., "Renal denervation prevents and reverses hyperinsulinemia-induced hypertension in rats," Hypertension 32, pp. 249-54 (1998).

Huang, S.K.S., et al. "Radiofrequency catheter ablation of cardiac arrhythmias: Basic concepts and clinical applications." 2nd ed. Armonk, NY: Futura Publishing Co. (2000).

Igawa, et al., "The Anatomical Features of the Junction between the Left Atrium and the Pulmonary Veins: The Relevance with Atrial Arrhythmia", Circulation, Journal of the American Heart Association, Abstracts from the 72nd Scientific Sessions, 100(18):I-285 (1999).

Jackman, W.M., et al. "Treatment of supraventricular tachycardia due to atrioventricular nodal reentry by radiofrequency catheter ablation of slow-pathway conduction." N England J Med, 327, 5:313-318 (Jul. 30, 1992).

Jain, M.K., et al. "A three-dimensional finite element model of radiofrequency ablation with blood flow and its experimental validation." Ann Biomed Eng, 28:1075-1084 (2000).

Jais, Pierre, M.D., "A Focal Source of Atrial Fibrillation Treated by Discrete Radiofrequency Ablation," Circulation, 95(3):572-576 (1996).

Janssen, B.J.A., et al. "Renal nerves in hypertension." Miner Electrolyte Metab, 15:74-82 (1989).

Kapural, L., et al. "Radiofrequency ablation for chronic pain control." Curr Pain Headache Rep, 5:517-525 (2001).

Kay, et al., "Radiofrequency Ablation for Treatment of Primary Atrial Tachycardia," Journal of the American College of Cardiology, 21(4):901-909 (1993).

Koepke, J.P., et al. "The physiology teacher: Functions of the renal nerves." The Physiologist, 28, 1:47-52 (1985).

(56) References Cited

OTHER PUBLICATIONS

Kompanowska-Jezierska, et al. "Early effects of renal denervation in the anaesthetised rat: Natriuresis and increased cortical blood flow," J Physiol, 531.2:527-534 (2001).
Krimholtz et al., "New Equivalent Circuits for Elementary Piezo-electric Transducers," Electronics Lettres, vol. 6, No. 13, pp. 398-399, Jun. 25, 1970.
Kumagai, et al., "Treatment of Mixed Atrial Fibrillation and Typical Atrial Flutter by Hybrid Catheter Ablation," Pacing and Clinical Electrophysiology, 23(11):1839-1842, Part 2 (2000).
Labonte, S. "Numerical model for radio-frequency ablation of the endocardium and its experimental validation." IEEE T Bio-med Eng, 41,2:108-115 (1994).
Lee, S.-J., et al. "Ultrasonic energy in endoscopic surgery," Yonsei Med J, 40:545-549 (1999).
Leertouwer, T.c., et al. "In-vitro validation, with histology, of intravascular ultrasound in renal arteries." J Hypertens, 17:271-277 (1999).
Lesh, M.D., "An Anatomic Approach to Prevention of Atrial Fibrillation: Pulmonary Vein Isolation with Through-the-Balloon Ultrasound Ablation (TTB-US)," Thorac. Cardiovasc. Surg. 47 (1999) (Suppl.) 347-51.
Lesh, Michael D., M.D., "Radiofrequency Catheter Ablation of Atrial Arrhythmias," Circulation, 89(3):1074-1089 (1994).
Liem, L. Bing, "In Vitro and In Vivo Results of Transcatheter Microwave Ablation Using Forward-Firing Tip Antenna Design," Pacing and Clinical Electrophysiology, Cardiostim '96 Proceedings, 19(11), Part 2 pp. 2004-2008 (1996).
Lin, Wei-Shiang, M.D., "Pulmonary Vein Morphology in Patients with Paroxysmal Atrial Fibrillation Initiated by Ectopic Beats Originating From the Pulmonary Veins," Circulation 101(11):1274-81, 2000.
Lowe, J.E. "Surgical treatment of the Wolff-Parkinson-White syndrome and other supraventricular tachyarrhythmias." J Card Surg, 1:117-134 (1986).
Lundin, S. et al. "Renal sympathetic activity in spontaneously hypertensive rats and normotensive controls, as studied by three different methods." Acta Physiol Scan, 120,2:265-272 (1984).
Lustgarten, D.L., et al. "Cryothermal ablation: Mechanism of tissue injury and current experience in the treatment of tachyarrhythmias," Progr Cardiovasc Dis, 41:481-498 (1999).
Mallavarapu, Christopher, "Radiofrequency Catheter Ablation of Atrial Tachycardia with Unusual Left Atrial Sites of Origin," Pacing and Clinical Electrophysiology, vol. 19(6), pp. 988-992 (1996).
McRury, I.D., et al. "Nonuniform heating during radiofrequency catheter ablation with long electrodes." Circulation, 96:4057-4064 (1997).
Mehdirad, A., et al. "Temperature controlled RF ablation in canine ventricle and coronary sinus using 7 Fr or 5 Fr ablation electrodes." PACE, 21:310-321 (1998).
Miller, B.F., and Keane, C.B. "Miller-Keane Encyclopedia & Dictionary of Medicine, Nursing, & Allied Health." Philadelphia: Saunders (1997) ("ablation").
Misaki, T., et al. "Surgical treatment of patients with Wolff-ParkinsonWhite syndrome and associated Ebstein's anomaly." J Thorae Cardiovase Surg, 110: 1702-1707 (1995).
Moak, J.P., et al. "Case report: Pulmonary vein stenosis following RF ablation of paroxysmal atrial fibrillation: Successful treatment with balloon dilation." J Intery Card Electrophys, 4:621-631 (2000).
Montenero, Sandro, Annibale, "Electrograms for Identification of the Atrial Ablation Site During Catheter Ablation of Accessory Pathways," Pacing and Clinical Electrophysiology, vol. 19(6), pp. 905-912 (1996).
Morrissey, D.M., "Sympathectomy in the treatment of hypertension." Lancet, CCLXIV:403-408 (1953).
Moubarak, Jean B., "Pulmonary Veins-Left Atrial Junction: Anatomic and Histological Study," Pacing & Clin. Electrophys. 23(11 pt. 2):1836-8, 2000.

Nakagawa, A., et al. "Selective ablation of porcine and rabbit liver tissue using radiofrequency: Preclinical study." Eur Surg Res, 31:371-379 (1999).
Nakagawa, H., et al. "Comparison of in vivo tissue temperature profile and lesion geometry for radiofrequency ablation with a saline-irrigated electrode versus temperature control in a eanine thigh muscle preparation." Circulation, 91 :2264-2273 (1995).
Nakagawa, H., et al. "Inverse relationship between electrode size and lesion size during radiofrequency ablation with active electrode cooling." Circulation, 98:458-465 (1998).
Neutel, J. M. "Hypertension and its management: A problem in need of new treatment strategies." JRAAS, I:S 1 O-S 13 (2000).
Nozawa, T., et al. "Effects of long-term renal sympathetic denervation on heart failure after myocardial infarction in rats." Heart Vessels, 16:51-56 (2002).
O'Connor, B.K., et al. "Radiofrequency ablation of a posteroseptal accessory pathway via the middle cardiac vein in a six-year-old child." PACE, 20:2504-2507 (1997).
Oliveira et al., "Renal Denervation Normalized Pressure and Baroreceptor Reflex in High Renin Hypertension in Conscious Rats," Hypertension Suppl. II vol. 19 No. 2 pp. 17-21 (1992).
Oral, H., et al. "Pulmonary vein isolation for paroxysmal and persistent atrial fibrillation." Circulation, 105: 1077-1081 (2002).
Page, I., et al. "The effect of renal denervation in the level of arterial blood pressure and renal function in essential hypertension." J Clin Invest, XIV:27-30 (1935).
Panescu, D., et al. "Radiofrequency multielectrode catheter ablation in the atrium." Phys Med Biol, 44:899-915 (1999).
Pavin, D., et al. "Permanent left atrial tachycardia: Radiofrequency catheter ablation through the coronary sinus." J Cardiovasc Electrophysiol, 12:395-398 (2002).
Peet, M., "Hypertension and its surgical treatment by bilateral supradiaphragmatic splanchnicectomy," Am. J. Surgery, pp. 48-68 (1948).g.
Petersen, H. H., et al. "Lesion dimensions during temperature controlled radiofrequency catheter ablation of left ventricular porcine myocardium: Impact of ablation site, electrode size, and convective cooling." Circulation, 99:319-325 (1999).
Pohl, M.A. "Renovascular hypertension and ischemic nephropathy" A chapter in a book edited by Sehrier, R.W. "Atlas of diseases of the kidney: Hypertension and the kidney." Blackwell Science (1999).
Prager, Nelson, A., "Long Term Effectiveness of Surgical Treatment of Ectopic Atrial Tachycardia," Journal of the American College of Cardiology, vol. 22(1):85-92 (1993).
Pugsley, M.K., et al. "The vascular system an overview of structure and function." J Pharmacol Toxical Methods, 44:333-340 (2000).
Rappaport et al. "Wide-Aperture Microwave Catheter-Based Cardiac Ablation", Proceedings of the First Joint BMES/EMBS Conference, Oct. 13-16, 1999, p. 314.
Reuter, David, M.D., et al., "Future Directions of Electrotherapy for Atrial Fibrillation," Journal of Cardiovascular Electrophysiology, 9(8):S202-S210 (1998).
Robbins, Ivan, M.D., "Pulmonary Vein Stenosis After Catheter Ablation of Atrial Fibrillation," Circulation, 98:1769-1775 (1998).
Sanderson, J.E., et al. "Effect of B-blockage on baroreceptor and autonomic function in heart failure." Clin Sei, 69:137-146 (1999).
Schauerte, P., et al. "Catheter ablation of cardiac autonomic nerves for prevention of vagal atrial fibrillation," Circulation, 102:2774-2780 (2000).
Scheinman, M. M., et al. "The 1998 NASPE prospective catheter ablation registry." PACE, 23:1020-1028 (2000).
Scheinman, Melvin M., "NASPE Survey on Catheter Ablation," 1995.
Smithwick et al., "Splanchnicetomy for Essential Hypertension," J. Am. Med. Assn. 152:16, pp. 1501-04 (1953).
Solis-Herruzo et al., "Effects Lumbar Sympathetic Block on Kidney Function in Cirrhotic Patients with Hepatorneal Syndrome," J. Hepatol. 5, pp. 167-173 (1987).
Stella, A., et al. "Effects of reversible renal denervation on hemodynamic and excretory functions of the ipsilateral and contralateral kidney in the cat," J Hypertension, 4:181-188 (1986).

(56) References Cited

OTHER PUBLICATIONS

Stellbrink, C., et al. "Transcoronary venous radiofrequency catheter ablation of ventricular tachycardia." J Cardiovasc Electropysiol 8:916-921 (1997).
Swain, et al., An endoscopically deliverable tissue-transfixing device for securing biosensors in the gastrointestinal tract, Gastrointestinal Endoscopy. 1994, 40:AB35.
Swartz, John F., "A Catheter-based Curative Approach to Atrial Fibrillation in Humans," Circulation, Abstracts from the 67th Scientific Sessions, Clinical Cardiology: Radio Frequency Ablation of Atrial Arrhythmias, 90(4), part 2, I-335 (1994).
Swartz, John F., M.D., "Radiofrequency Endocardial Catheter Ablation of Accessory Atrioventricular Pathway Atrial Insertion Sites," Circulation, 87:487-499 (1993).
Takahashi, H., et al. "Retardation of the development of hypertension in DOCA-salt rats by renal denervation." Jpn Circ J, 48:567-574 (1984).
Tanaka et al., "A new radiofrequency thermal balloon catheter for pulmonary vein isolation," Journal of the American College of Cardiology 38(7): 2079-86, Dec. 2001.
Tracy, Cynthia M., "Radiofrequency Catheter Ablation of Ectopic Atrial Tachycardia Using Paced Activation Sequence Mapping," J. of the Amer. College of Cardiol. 21(4):910-7, 1993.
Tungjitkusolmun, S. "Ablation." A chapter in a book edited by Webster, J. G., "Minimally invasive medical technology." Bristol UK: IOP Publishing, 219 (2001).
Uchida, F., et al. "Effect of radio frequency catheter ablation on parasympathetic denervation: A comparison of three different ablation sites," PACE, 21:2517-2521 (1998).
Uflacker, R., "Atlas of vascular anatomy: An angiographic approach." Baltimore: Williams & Wilkins, 424 (1997).
Valente, J. F. "Laparoscopic renal denervation for intractable ADPKD-related pain," Nephrol Dial Transplant, 16:160 (2001).
Van Hare, G. F., et al. "Percutaneous radiofrequency catheter ablation for supraventricular arrhythmias in children." JACC, 17:1613-1620 (1991).
Van Hare, George F., "Radiofrequency Catheter Ablation of Supraventricular Arrhythmias in Patients With Congenital Heart Disease: Results and Technical Considerations," J. of the Amer. College of Cardiol. 22(3):883-90, 1993.
Volkmer, Marius, M.D., "Focal Atrial Tachycardia from Deep Inside the Pulmonary Veins," PACE vol. 20:533, p. 1183 (1997).
Vujaskovie, Z., et al. "Effects of intraoperative hyperthermia on canine seiatie nerve: Histopathology and morphometric studies." Int JHyperthermia, 10,6:845-855 (1994).
Walsh, Edward P., M.D., "Transcatheter Ablation of Ectopic Atrial Tachycardia in Young Patients Using Radiofrequency Current," Circulation, 86(4):1138-1146 (1992).
Weinstock, M., et al. "Renal denervation prevents sodium retention and hypertension in salt-sensitive rabbits with genetic baroreflex impairment," Clinical Science, 90:287-293 (1996).
Weir, M. R., et al. "The renin-angiotensin-aldosterone system: A specific target for hypertension management." Am J Hypertens,12:205S-213S (1999).
Yamamoto, T., et al. "Blood velocity profiles in the human renal artery by Doppler ultrasound and their relationship to atherosclerosis." Arterisocl Throm Vas, 16: 172-177 (1996).
Zhang et al., "The development of a RF electrical pole catheter for heart ablation," China Academic Journal Electronic Publishing House 23(5): 279-80, Sep. 1999 (With English Abstract).
Zipes, Douglas P., M.D., "Catheter Ablation of Arrhythmias," 1994.

\* cited by examiner

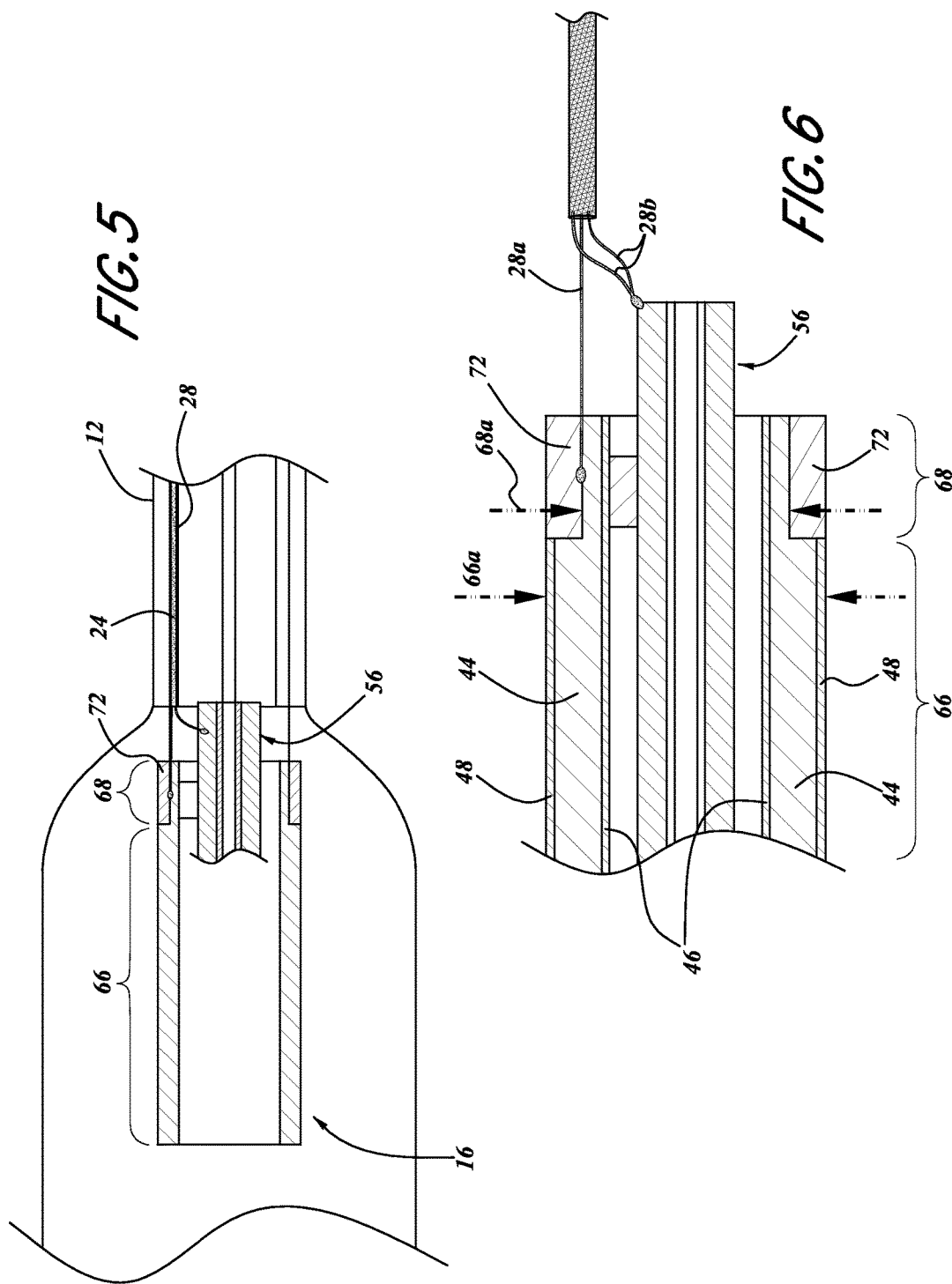

ULTRASOUND-BASED NEUROMODULATION SYSTEM

CROSS-REFERENCE TO RELATED APPLICATIONS

This application claims the priority benefit under 35 U.S.C. § 119(e) of U.S. Provisional Application No. 61/784,790, filed Mar. 14, 2013, the entirety of which is hereby incorporated by reference herein.

BACKGROUND

Field

This application relates generally to minimally-invasive devices, systems and methods of energy delivery to a targeted anatomical location of a subject, and more specifically, to catheter-based, intraluminal devices and systems configured to emit ultrasonic energy for the neuromodulation (e.g., ablation, necrosing, etc.) of nerve tissue.

Description of the Related Art

Catheter-based energy delivery systems can be used to access and treat portions of a subject's anatomy minimally-invasively. Such systems can be advanced through a subject's vasculature to reach a target anatomical site. The various embodiments disclosed herein provide improved devices, systems and methods related to energy delivery within a subject.

SUMMARY

According to some embodiments, an intravascular, ultrasound-based ablation system includes a catheter comprising a guidewire lumen, at least one cable lumen and at least one fluid lumen, and a balloon or other expandable structure or member positioned at a distal end of the catheter, wherein an interior of the balloon is in fluid communication with the at least one fluid lumen of the catheter. In some embodiments, the balloon is configured to inflate when fluid (e.g., cooling fluid) is delivered into the interior through the at least one fluid lumen of the catheter. The system further comprises a tip extending distally from a distal end of the balloon, wherein the tip comprises an internal guidewire passage, and one or more ultrasound transducers positioned within the balloon. In some embodiments, the ultrasound transducer includes a cylindrical tube with inner and outer surfaces, each of the inner and outer surfaces comprising an electrode, wherein the ultrasound transducer defines an internal space adjacent the inner electrode surface, the internal space being in fluid communication with the interior cavity of the balloon so that, when in use, fluid entering the balloon passes along both the inner and outer surfaces to transfer heat away from the ultrasound transducer.

In some embodiments, at least one electrical cable (e.g., coaxial cable) is routed or otherwise positioned within the at least one cable lumen of the catheter, wherein the at least one electrical cable is electrically coupled to the electrodes along the inner and outer surfaces of the ultrasound transducer. The system further includes a backing member or post extending from the catheter to the tip and connecting the catheter with the tip. In some embodiments, the backing member is positioned within the internal space of the ultrasound transducer, wherein the backing member comprises a central opening that is generally aligned with the guidewire lumen of the catheter and the internal guidewire passage of the tip to permit the system to be delivered to a desired vascular position over a guidewire. In some embodiments, the backing member serves as a fluid barrier between fluid circulated within the balloon interior and the central opening.

According to some embodiments, the backing member comprises an electrically insulating material (e.g., polyimide, another polymeric material, etc.) along an interior surface of the central opening of the backing member so as to prevent electrical conduction between a guidewire and the backing member. In some embodiments, the guidewire lumen extends from a proximal end of the catheter to the balloon. In other embodiments, the guidewire lumen extends from a location between the proximal and distal ends of the catheter to the distal end of the catheter, such that the catheter comprises a rapid exchange design.

According to some embodiments, an intravascular, ultrasound-based ablation system comprises a catheter having at least one cable lumen and at least one fluid lumen, a balloon or other expandable structure positioned at a distal end of the catheter, an interior of the balloon being in fluid communication with the at least one fluid lumen of the catheter and an ultrasound transducer positioned within the balloon, wherein the ultrasound transducer comprises a cylindrical tube having a proximal end and a distal end and inner and outer surfaces. In some embodiments, each of the inner and outer surfaces comprises an electrode, wherein the proximal end of the cylindrical tube comprising a stepped portion, and wherein a portion of the outer diameter formed by the outer surface of the cylindrical tube is smaller than a portion of the outer diameter of the cylindrical tube located distal to the stepped portion. The system further comprises at least one electrical cable positioned within the at least one cable lumen of the catheter, the at least one electrical cable being configured to supply electrical power to the ultrasound transducer, wherein the at least one electrical cable comprises a first conductor and a second conductor.

In some embodiments, the system further comprises one or more a stand-off assemblies located within an interior and along or near the proximal end of the cylindrical tube of the ultrasound transducer. In one embodiment, the stand-off assembly is electrically conductive and in contact with, at least intermittently, the electrode along the inner surface of the cylindrical tube of the ultrasound transducer, wherein the first conductor is connected to an exterior of the cylindrical tube along the stepped portion, and wherein the second conductor is connected to the stand-off assembly so that the second conductor is electrically coupled to the electrode along the inner surface of the cylindrical tube. The system further comprise a ring surrounding the stepped portion of the cylindrical tube, the ring being sized and shaped to surround the portion of the outer diameter of the cylindrical tube located distal to the stepped portion, wherein the ring is electrically conductive so that the first connector is electrically coupled to the electrode along the outer surface of the cylindrical tube, and wherein the ring allows for more uniform electrical loading of the ultrasound transducer when the electrical transducer is energized.

According to some embodiments, the ring comprises conductive solder. In some embodiments, the ring comprises a conductive machined ring or other member or feature that couples around the stepped portion of the cylindrical tube. In some embodiments, the stepped portion extends approximately 5% to 25% of a length of the cylindrical tube. In one embodiment, the stepped portion comprises a portion of the cylindrical tube that is removed using grinding or other removal techniques. In some embodiments, an impedance of the at least one electrical cable substantially matches an impedance of the ultrasound transducer. In some embodiments, the impedance of the electrical cable and the ultrasound transducer is approximately 40 to 60 ohms (e.g., 50 ohms).

According to some embodiments, an intravascular, ultrasound-based ablation system comprises a catheter having a cable lumen extending from a proximal end to a distal end of the catheter, an ultrasound transducer positioned at or near a distal end of the catheter, wherein the ultrasound transducer comprises a cylindrical tube with inner and outer surfaces, wherein each of the inner and outer surface comprising an electrode. The system further comprises a backing member or post extending from the distal end of the catheter and positioned within an interior of the ultrasound transducer, wherein the backing member is configured to support the ultrasound transducer, and wherein the backing member is electrically coupled to the electrode along the inner surface of the cylindrical tube of the ultrasound transducer. In some embodiments, the system comprises an electrical cable positioned within the cable lumen of the catheter and extending from the proximal end to the distal end of the catheter, wherein a proximal end of the electrical cable is coupled to a generator configured to selectively provide electrical power to the ultrasound transducer through the electrical cable. In one embodiment, the electrical cable comprises a first electrical connector and a second electrical connector, wherein the first connector is electrically coupled to the electrode along the outer surface of the ultrasound transducer, and wherein the second connector is electrically coupled to the backing member and the electrode along the inner surface of the ultrasound transducer. In some embodiments, an impedance of the electrical cable is substantially equal to an impedance of the ultrasound transducer, thereby providing a more efficient power transfer from the generator to the ultrasound transducer when the ablation system is in use.

According to some embodiments, the electrical cable comprises a coaxial cable. In one embodiment, the backing member or post comprises at least one stand-off assembly that electrically couples the backing member to the electrode along the inner surface of the cylindrical tube of the ultrasound transducer. In some embodiments, the backing member or post is coupled to both the proximal and the distal ends of the transducer. In some embodiments, the impedance of the electrical cable and the ultrasound transducer is approximately 40 to 60 ohms (e.g., approximately 50 ohms). In some embodiments, the first connector of the electrical cable is electrically coupled to the electrode while not physically attached to the outer surface of the ultrasound transducer.

According to some embodiments, an intravascular, ultrasound-based ablation system includes a catheter comprising at least one fluid lumen, a balloon or other expandable member positioned at a distal end of the catheter, wherein an interior of the balloon is in fluid communication with the at least one fluid lumen of the catheter, and wherein the balloon is configured to inflate when fluid is delivered into the interior through the at least one lumen of the catheter. The system further comprises an ultrasound transducer positioned within the balloon, wherein the ultrasound transducer includes a cylindrical tube with inner and outer surfaces, wherein each of the inner and outer surface comprising an electrode. In some embodiments, the ultrasound transducer defines an internal space adjacent the inner electrode surface, wherein the internal space is in fluid communication with the interior cavity of the balloon so that, when in use, fluid entering the balloon passes along both the inner and outer surfaces to cool the ultrasound transducer. In some embodiments, the system additionally comprises a fluid transfer device configured to selectively deliver a cooling fluid within the balloon when the ultrasound transducer is activated in order to transfer heat away from the ultrasound transducer during use, wherein the fluid transfer device comprises a reservoir for storing a volume of cooling fluid and a movable member configured to move within an interior of the reservoir in order to transfer cooling fluid through the at least one fluid lumen of the catheter to the balloon, and wherein the reservoir is sized to store sufficient cooling fluid for an entire ablation procedure.

According to some embodiments, the movable member is coupled to a motor for selectively advancing the movable member relative to the reservoir. In one embodiment, the motor comprises a stepper motor or another type of motor. In some embodiments, the fluid transfer device comprises a syringe pump. In some embodiments, the catheter comprises a fluid delivery lumen and a fluid return lumen, wherein cooling fluid is delivered to the balloon from the fluid transfer device via the fluid delivery lumen, and wherein cooling fluid is withdrawn from the balloon via the fluid return lumen. In some embodiments, the fluid transfer lumen is in fluid communication with a first fluid transfer device, and wherein the fluid return lumen is in fluid communication with a second fluid transfer device, wherein both the first and the second fluid transfer devices are operated simultaneously to circulate cooling fluid through the balloon during an ablation procedure. In some embodiments, the fluid transfer device is configured to deliver cooling fluid through the at least one fluid lumen of the catheter and into the balloon at a flowrate of 30-50 ml/min (e.g., about 40 ml/min).

A method of intraluminally ablating or otherwise neuromodulating nerve tissue using an ultrasound-based ablation system includes advancing a catheter of the ablation system intraluminally to a target anatomical location of a subject, wherein the system comprises a balloon positioned at a distal end of the catheter, an interior of the balloon being in fluid communication with at least one fluid delivery lumen and at least one fluid return lumen of the catheter, wherein an ultrasound transducer is positioned within the interior of the balloon. The method further includes circulating cooling fluid through the interior of the balloon by transferring cooling fluid from a fluid transfer device through the at least one fluid lumen of the catheter and transferring cooling fluid away from the interior of the balloon through the at least one fluid return lumen and activating the ultrasound transducer positioned within the balloon to ablate nerve tissue adjacent to the target anatomical location of the subject. In some embodiments, cooling fluid is circulated adjacent the ultrasound transducer within the balloon when the ultrasound transducer is activated. In some embodiments, the fluid transfer device comprises a reservoir for storing a volume of cooling fluid and a movable member configured to move within an interior of the reservoir in order to transfer cooling fluid through the at least one fluid lumen of the catheter to the balloon, wherein the reservoir is sized to store sufficient cooling fluid for an entire ablation procedure.

According to some embodiments, the movable member (e.g., plunger) is coupled to a motor for selectively advancing the movable member relative to the reservoir. In one embodiment, the motor comprises a stepper motor or another type of motor or actuator. In some embodiments, the fluid transfer device comprises a syringe pump or another type of pump. In some embodiments, cooling fluid is circulated through the balloon at a flowrate of 30-50 ml/min (e.g., about 40 ml/min).

According to some embodiments, a coupling configured for use in an outlet of a fluid container (e.g., IV bag) includes a hub configured to abut against the outlet of the coupling, wherein the hub is configured to prevent over-insertion of the coupling into the fluid container. In some embodiments, a proximal end of the hub comprises a fitting configured for attachment to a fluid conduit. The coupling further comprises a spike portion extending distally from the hub, wherein a length of the spike is 0.5 inches to 3 inches. In some embodiments, the coupling comprises at least two fluid lumens (e.g., 2, 3, 4, 5, more than 5, etc.) that extend throughout an entire length of the coupling from the proximal end of the hub to a distal end of the spike, wherein the lumens place an interior of the fluid container in fluid communication with at least one fluid conduit secured to the hub. In some embodiments, the coupling permits at two different fluid sources to be placed in fluid communication with an interior of a fluid container comprising only a single outlet. In some embodiments, such a coupling or spike can be used on an IV bag or other fluid container that is placed in fluid communication with a syringe pump of a treatment system. Thus, the IV bag can be configured to store additional fluid that will be delivered through a delivery lumen into a balloon and/or can be configured to store excess fluid being returned from the balloon via a return lumen in the catheter. Thus, the coupling can be placed in fluid communication with the catheter and/or the syringe pump of the treatment system.

In some embodiments, the spike includes a taper along at least a portion of its length, so that a cross-sectional dimension of the spike is smaller along the distal end of the spike than a cross-sectional dimension of the spike along a proximal end of the spike. In some embodiments, the spike comprises a cone-shaped, with either a linear or non-linear (e.g., curved) profile. In some embodiments, the spike is configured for placement into an IV bag comprising only a single outlet or port. In some embodiments, the coupling comprises two fluid lumens.

BRIEF DESCRIPTION OF THE DRAWINGS

FIG. 5 illustrates a partial cross-sectional view of the expandable member and ultrasound transducer according to one embodiment.

FIG. 6 illustrates a partial cross-sectional view of the ultrasound transducer of FIG. 5.

DETAILED DESCRIPTION

Figure 1:
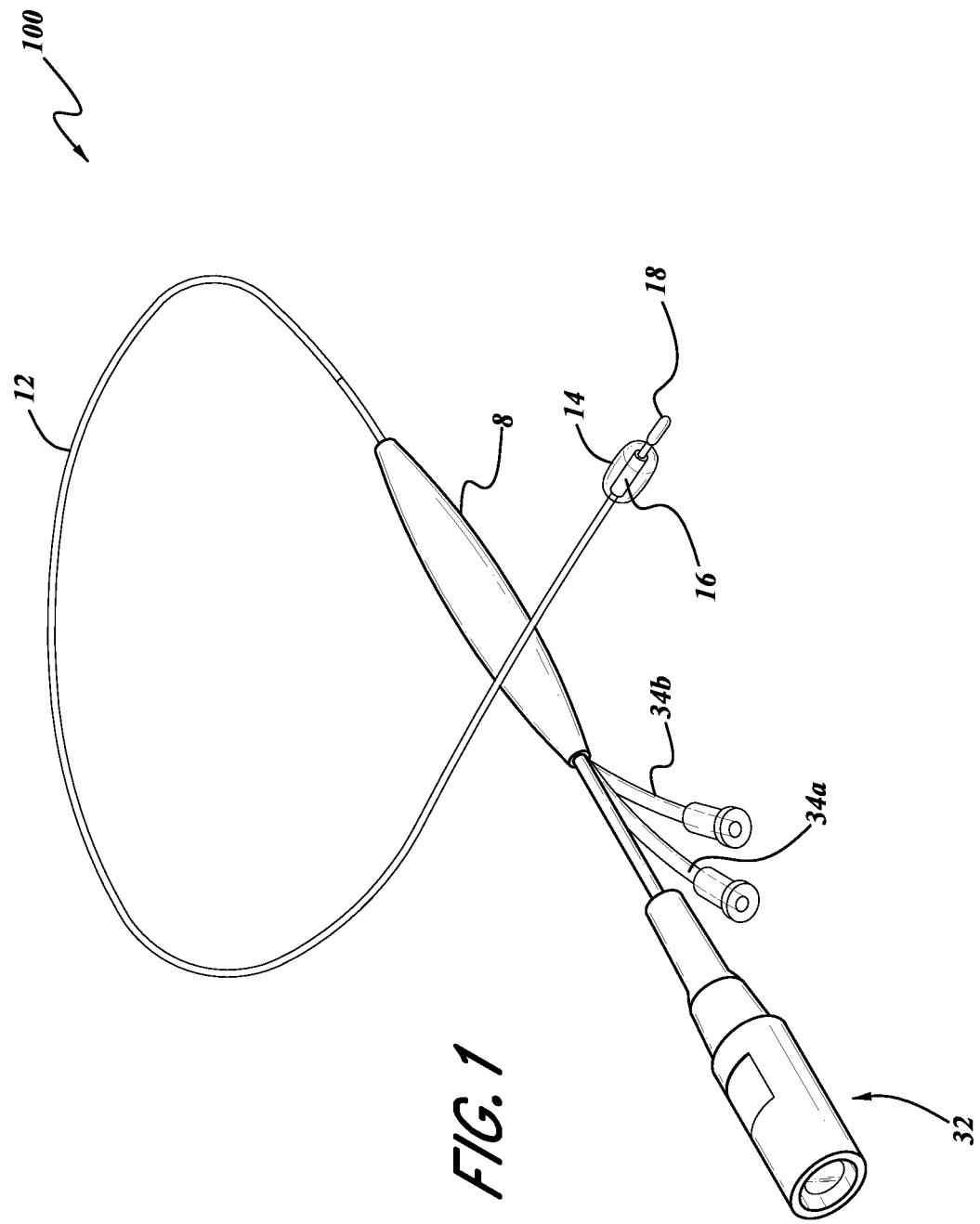
FIG. 1 illustrates an ultrasound-based treatment system according to one embodiment.

In the various embodiments described herein, catheter-based systems and methods for treating targeted tissue of a subject are disclosed. The systems and methods are particularly useful in neuromodulation procedures (e.g., denervation). For example, as discussed in greater detail herein, the systems can be used to target select nerve tissue of the subject. Targeted nerve tissue can be heated by the application of ultrasonic energy thereto in order to neuromodulate (e.g., ablate, necrose, stimulate, etc.) the tissue. In other embodiments, the application of ultrasonic energy can be used to target other adjacent tissue of a subject, either in lieu of or in addition to nerve tissue. Accordingly, the systems and methods disclosed herein can be used to treat hypertension, other nerve-mediated diseases and/or any other ailment. The systems and methods disclosed herein can also be used in ablative procedures of non-nerve tissue (including, but not limited to, tumors, cardiac tissue, and other tissue types). Arrhythmias are treated according to one embodiment.

The catheter-based systems disclosed herein can be delivered intraluminally (e.g., intravascularly) to a target anatomical region of the subject, such as, for example, the renal artery, another targeted vessel or lumen, etc. Once properly positioned within the target vessel, the ultrasound transducer can be activated to selectively deliver acoustic energy radially outwardly from a distal end of the system and toward the targeted tissue. The transducer can be activated for a particular time period and at a particular energy level (e.g., power, frequency, etc.) in order to accomplish the desired effect on the targeted tissue. In embodiments where the targeted tissue is nerve tissue, the systems are configured to deliver ultrasonic energy through the adjacent wall of the vessel in which the system is positioned. For example, with respect to the renal artery, targeted nerve tissue is typically located about 0.5 mm to 8 mm (e.g., 1 mm to 6 mm) from the vessel wall. Accordingly, ultrasonic energy can be used to heat the nerve tissue in order to at least partially neuromodulate the nerve tissue. As used herein, neuromodulation shall be given its ordinary meaning and shall include, without limitation, complete or partial ablation, necrosis, stimulation and/or the like. In some embodiments, the acoustic energy is delivered radially outwardly from the ultrasound transducer, permitting the delivery of ultrasonic energy to target nerve tissue regardless of the radial orientation of such nerve tissue relative to a vessel (e.g., renal artery). Further, as discussed in greater detail herein, the various systems disclosed herein can be configured to deliver a cooling fluid to the anatomical region being treated in order to protect certain tissue of the subject (e.g., to prevent or reduce the likelihood of stenosis or other damage to the wall of the vessel through which energy is delivered during a procedure).

General System Components and Features

Figure 2:
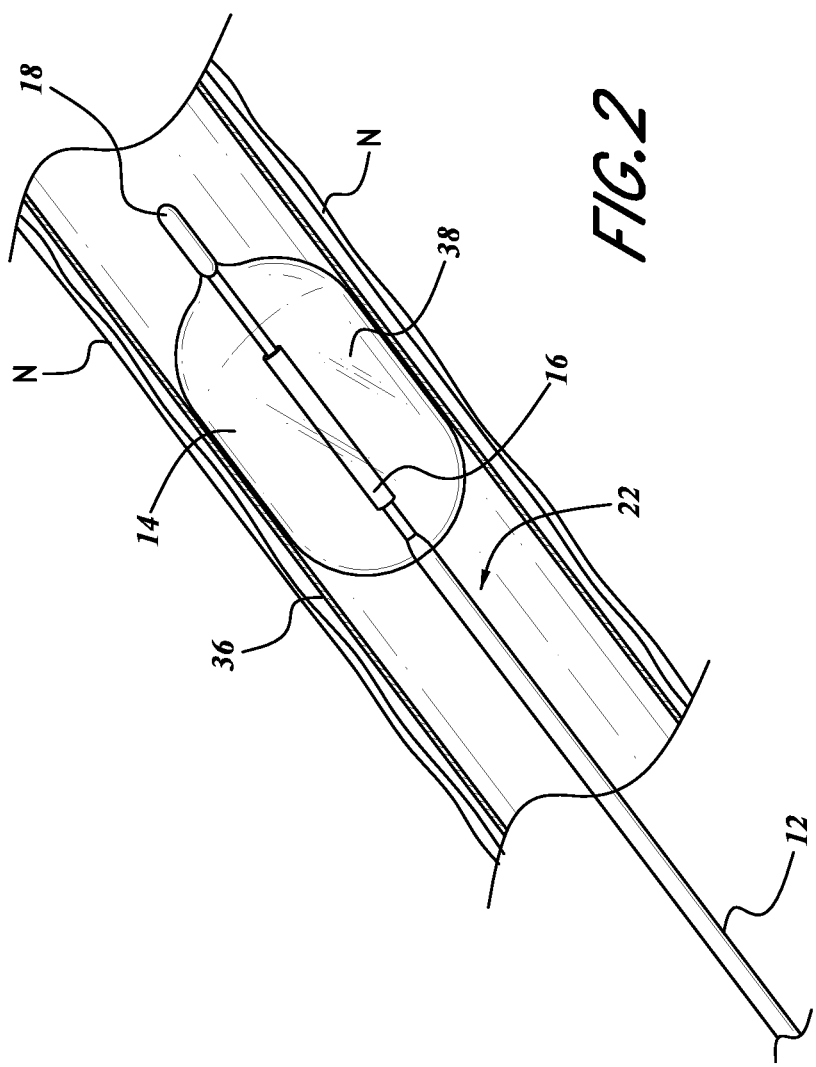
FIG. 2 illustrates a detailed side view of a distal end of the system depicted in FIG. 1.

FIGS. 1 and 2 illustrate an ultrasound-based ablation system 100 according to one embodiment. As shown, the system 10 can comprise a catheter 12 having a proximal end 20 and a distal end 22, an expandable member 14 (e.g., balloon) along the distal end of the catheter and one or more ultrasound transducers 16 positioned within the expandable member 14. A proximal portion of the system can comprise a handle 8 and one or more connectors or couplings (e.g., an electrical coupling 32 for connecting the system to a power generator, one or more ports 34 for placing the system in fluid communication with a cooling fluid, etc.).

In some embodiments, the catheter 12 includes one or more lumens that can be used as fluid conduits, electrical cable passageways, guidewire lumen and/or the like. For example, as illustrated in FIG. 5, the catheter 12 can include at least one cable lumen 24 that is shaped, sized and otherwise configured to receive an electrical cable 28 (e.g., coaxial cable, wire, other electrical conductor, etc.). The electrical cable 28 advantageously permits the electrode of the system's ultrasound transducer to be selectively activated in order to emit acoustic energy to a subject.

The catheter 12 can also include at least one fluid lumen 26 for transferring cooling fluid (e.g., water, saline, other liquids or gases, etc.) to and from the balloon or other expandable member 14 located at the distal end of the system. As discussed in greater detail herein, in some embodiments, the catheter comprises at least two fluid lumens 26, one for delivering cooling fluid to the balloon and the other for returning the cooling fluid from the balloon. However, the catheter 12 can include only a single fluid lumen or more than two fluid lumen (e.g., 3, 4, more than 4, etc.), as desired or required.

Figure 3:
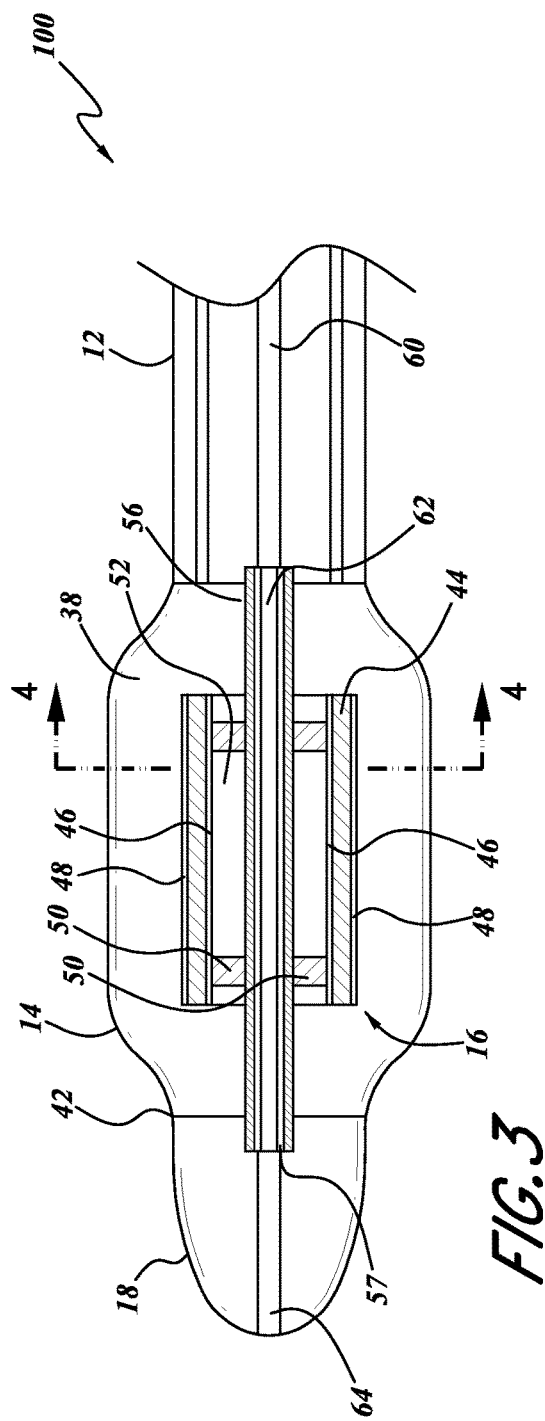
FIG. 3 illustrates a side cross-sectional view of the distal end of an ultrasound-based system according to one embodiment.

As illustrated in FIGS. 2 and 3, the ultrasound transducer 16 can be positioned completely within an interior of the expandable member 14 (e.g., balloon). In some embodiments, as shown in FIG. 2, when expanded, the outer wall of the balloon 14 is generally parallel with the walls of the cylindrical ultrasound transducer 16. The balloon 14 can be a compliant, semi-compliant or non-compliant medical balloon, as desired or required. In some embodiments, the ultrasound transducer 16 is liquid cooled along both its outer and inner electrodes, meaning that cooling liquid entering the balloon 14 is permitted to pass across both the exterior and interior surfaces of the cylindrical transducer to transfer heat away from the transducer. The transducer 16 can include a reflective interface (e.g., along its interior) so as to permit ultrasonic energy generated at the inner electrode (e.g. along the interior surface of the cylindrical transducer) to be reflected radially outwardly.

Additional details regarding possible ultrasonic transducer designs and embodiments (e.g., both structurally and operationally) and/or catheter-based ultrasound delivery systems are provided in U.S. patent application Ser. No. 11/267,123, filed on Jul. 13, 2001 and published as U.S. Publ. No. 2002/0068885 on Jun. 6, 2002; U.S. patent application Ser. No. 09/905,227, filed Jul. 13, 2001 and issued as U.S. Pat. No. 6,635,054 on Oct. 21, 2003; U.S. patent application Ser. No. 09/904,620, filed on Jul. 13, 2001 and issued as U.S. Pat. No. 6,763,722 on Jul. 20, 2004; U.S. patent application Ser. No. 10/783,310, filed Feb. 20, 2004 and issued as U.S. Pat. No. 7,837,676 on Nov. 23, 2010; U.S. patent application Ser. No. 12/227,508, filed on Feb. 3, 2010 and published as U.S. Publ. No. 2010/0130892 on May 27, 2010; U.S. patent application Ser. No. 10/611,838, filed on Jun. 30, 2003 and published as U.S. Publ. No. 2004/0082859 on Apr. 29, 2004; and PCT Appl. No. PCT/US2011/025543, filed on Feb. 18, 2011 and published as PCT Publ. No. WO 2012/112165 on Aug. 23, 2012. The entireties of all the foregoing applications is hereby incorporated by reference herein and made a part of the present application.

With continued reference to FIG. 1, one or more electrical cables that supply electrical power to the transducer 16 can be coupled via the electrical coupling 32 located at the proximal end of the system. In some embodiments, the electrical coupling comprises a standard or non-standard connection to a power supply and controller (not illustrated). For example, in some embodiments, the electrical coupling 32 can be easily and quickly attached and detached to a power supply and controller. As is described in greater detail below, the fluid lumen(s) 26 of the catheter can be used selectively transfer fluid (e.g., cooling fluid) between a fluid transfer device (e.g., fluid pump) and the interior of the balloon or other expandable member 14. The cooling fluid can be used to inflate the expandable member 14 and to provide cooling when the ultrasound transducer 16 is activated in order to transfer heat away from the ultrasound transducer 16 and/or the surrounding tissue of the subject during use.

The system 100 can be delivered to the target anatomical location (e.g., a renal artery) via femoral, radial or other intravascular access. The system can be delivered through the vasculature or other lumen of the subject either with or without the assistance of a guidewire. Accordingly, as discussed in greater detail below, the catheter and other components of the system can include a guidewire lumen or other passages to permit delivery over a guidewire.

In some embodiments, the ultrasonic transducers are operated in a range of from 1 to 20 MHz (e.g., 1-5 MHz, 5-10 MHz, 10-15 MHz, 15-20 MHz, 8-10 MHz, other values or ranges within the foregoing, etc.). In one embodiment, for example, the ultrasound transducer of the system is configured to operate at a frequency of about 9 MHz. In other embodiments, however, the frequency at which a transducer is operated can be below 1 MHz or above 20 MHz. The power supplied to the ultrasound transducer can vary, as desired or required, and in some embodiments, is 5 to 80 Watts (e.g., 5 to 50, 5 to 10, 10 to 20, 20 to 30, to 40, 40 to 50, 50 to 60, 60 to 70, 70 to 80 Watts, etc.) at the transducer. As noted above, the period of time during which the ultrasound is activated for a particular treatment procedure can vary, and can also depend on one or more other factors, such as, for example, the power level at the transducer, the frequency of ultrasonic energy emitted, the size of the vessel or other tissue being treated, the age, weight and gender of the patient being treated and/or the like. However, in some embodiments, the ultrasonic transducer is activated for about 10 seconds to 5 minutes (e.g., 30 seconds to 5 minutes, 1 to 3 minutes, about 2 minutes, 10 seconds to 1 minute, 1 to 2 minutes, 2 to 3 minutes, 3 to 4 minutes, 4 to 5 minutes, etc.).

Referring now to FIG. 2, in several embodiments, the system can be delivered intravascularly through a subject so that the transducer is positioned within a target vessel (e.g., a renal artery) 36 and adjacent nerve tissue N to be neuromodulated. As shown, the expandable member (e.g., balloon) 14 can inflated (e.g., using cooling fluid). Expansion of the balloon 14 can cause the wall of the balloon to at least partially engage the adjacent interior wall of the vessel 36. In addition, in some embodiments, expansion of the balloon or other expandable member 14 causes the transducer 16 to be generally centered within the vessel. The ultrasound transducer 16 can be activated to generate ultrasonic energy that passes radially outwardly through the balloon and to the adjacent tissue of the subject. For example, the ultrasonic or acoustic energy can pass through the wall of the vessel 36 and heat the adjacent nerve tissue N. In some embodiments, sufficient energy is delivered to the nerve tissue N to cause a desired heating and/or other response. Thus, the energy delivered to the nerve tissue can neuromodulate (e.g., necrose, ablate, stimulate, etc.) the nerves, as desired or required.

Guidewire-Enabled Catheter System

As noted above, the ultrasound treatment systems described herein can be configured to be delivered to a target anatomical location of a subject with or without the use of a guidewire. FIG. 3 illustrates a cross-sectional view of the distal end of an ultrasound-based ablation system 100 that is configured to be delivered over a guidewire. As shown, the ultrasound transducer 16 can comprise a cylindrical tube 44 comprising a piezoelectric material (e.g., PZT, lead zirconate titanate, etc.) with inner and outer electrodes 46, 48 along the inner and outer surfaces of the cylindrical tube 44, respectively. When activated, the piezoelectric material vibrates transverse to the longitudinal direction of the cylindrical tube 44 (e.g., radially).

With continued reference to FIG. 3, the transducer 16 is generally supported within the interior of the balloon 14 using a backing member or post 56. As shown, such a backing member 56 can extend from the catheter 12 to a distal tip 18. For example, in some embodiments, the backing member 56 is positioned within adjacent openings of the catheter and tip. Further, the balloon or other expandable member 14 can be secured along an exterior or other portion of the catheter and tip.

In order to permit liquid cooling along both the inner and outer electrodes 46, 48, the transducer can include one or more stand-off assemblies 50. As shown schematically in FIGS. 3 and 4, for example, the stand-off assemblies 50 can be positioned along each end of the transducer and couple the cylindrical portion of the transducer 16 to the backing member 56. The stand-off assemblies can define annular openings 55 through which cooling fluid may enter the interior space 52 of the cylindrical tube. The stand-off assembly 50 can be electrically conductive so as to electrically couple the inner electrode 46 of the transducer 16 to the backing member or post 56. As discussed in greater detail herein, for example, in some embodiments, one or more conductors of the electrical cable 28 can be electrically coupled to the backing member 56. Thus, as the power generator is activated, current can be delivered from the cable 28 to the inner electrode 46 of the transducer via the post 56 and the stand-off assembly 50. According to one embodiment, this advantageously eliminates the need to electrically couple the cable directly to the inner electrode of the transducer.

Figure 4:
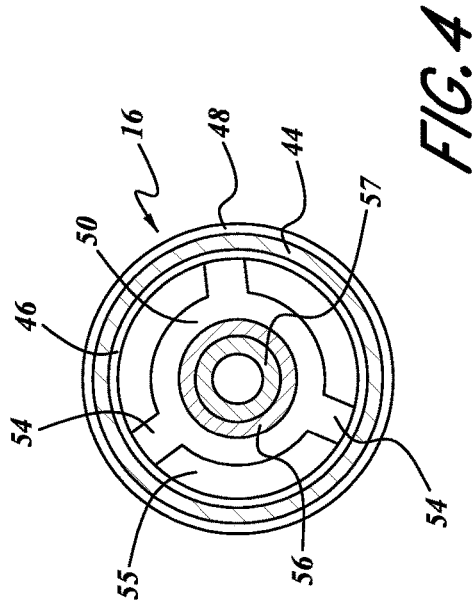
FIG. 4 illustrates a section view across a portion of the system of FIG. 3.

With reference to FIG. 4, the stand-off assembly 50 can have a plurality of ribs or attachment points 54 that engage the inner electrode 46. The number, dimensions and placement of the ribs 54 can vary, as desired or required. For example, in some embodiments, as illustrated in FIG. 4, a total of three ribs 54 are generally equally-spaced apart from one another at an angle of 120°.

With further reference to FIG. 3, the internal space 52 defined by the ultrasound transducer 16 can allow the piezoelectric material to vibrate both outwardly and inwardly in the transverse direction. As discussed herein, the internal space 52 of the transducer can be in fluid communication with the interior cavity 38 of the expandable member 14 so that, when in use, fluid entering the expandable member 14 can pass along and cool both the inner and outer surfaces of the ultrasound transducer 44. The cooling fluid can be used to maintain a desired temperature threshold along the interior wall of the vessel (e.g., renal artery) while allowing a higher temperature profile a particular distance radially away from the vessel wall. This permits targeted nerve tissue to be neuromodulated (e.g., necrosed, ablated, etc.) while protecting the vessel wall from unwanted harm or injury (e.g., stenosis, ablation or reconstruction, scarring, etc.). Likewise, for embodiments that treat tissue other than nerves, target tissue can be treated, while protecting non-target tissue.

According to some embodiments, as illustrated in FIGS. 3 and 4, the ultrasound-based ablation system 100 can be configured for delivery over a guidewire (e.g., regular guidewire, rapid-exchange system, etc.). Thus, the catheter can include a central guidewire lumen 60. In addition, other portions of the system can also include a lumen or other passage for receiving a guidewire. For example, the backing member or post 56 and the tip 18 can each comprise a central opening, lumen or passage 62, 64 that are generally aligned with the guidewire lumen 60 of the catheter. In one embodiment, the guide wire lumen 60 of the catheter 12 extends from the proximal end 20 of the catheter to the distal tip 18. Alternatively, a monorail guidewire configuration could be used, where the catheter rides on the wire just on the tip section distal to the transducer. In another embodiment, the guidewire lumen 58 extends from a location between the proximal 20 and distal 22 ends of the catheter to the distal end 22 of the catheter, such that the catheter comprises a rapid exchange design (e.g., where the guidewire lumen of the catheter does not extend to the proximal end of the catheter). In any of the embodiments disclosed herein, regardless of whether or not the system is configured for delivery over a guidewire, the catheter could comprise one or more pull wires or other features that permit the system to be selectively manipulated (e.g., for selective deflection of the catheter) to aid in the delivery and placement within the subject.

The backing member 56 can advantageously serve as a fluid barrier between the cooling fluid circulated within the expandable member 14 and the central opening, lumen or passage 62 through which the guidewire is routed. In some embodiments, the backing member or post 56 can include one or more layers of an electrically insulating material or member 57 (e.g., polyimide) along an interior surface of the central opening 62 of the backing member 56 so as to prevent electrical conduction between the guidewire 58 and the backing member 56. Such an electrically insulating member 57 can also provide one or more other benefits to the system, such as, for example, reduced friction between the guidewire and the post. As illustrated in FIG. 3, the various lumens or other openings of the catheter 12, backing member or post 56 and the distal tip 18 can be generally aligned and approximately sized and shaped so at to allow a guidewire to freely and easily pass therethrough.

Electrical Loading of Transducer

FIG. 5 illustrates a partial cross-sectional view of the expandable member (e.g., balloon) 14 and ultrasound transducer 16 of an ultrasound-based ablation system 100 according to one embodiment. As shown in FIG. 5, in some embodiments, the ultrasound transducer 16 comprises a uniform and cylindrical outer and inner diameters to provide for a more uniform distribution of acoustic energy radially emanating therefrom (e.g., toward adjacent nerve tissue surrounding a vessel). Such a configuration can help ensure that a generally equal acoustic energy profile is delivered by the transducer during use. Accordingly, localized hotspots of ultrasonic energy, where a greater amount of heating is observed along one circumferential area and/or longitudinal area of the treatment region, are eliminated or reduced. Further, as noted herein, adjacent portions of the balloon or other expandable member 14 can also include a uniform and/or flat profile upon expansion, such that outer and inner surfaces of the cylindrical transducer are generally parallel with the wall of the expanded balloon. Such a feature can help ensure that acoustic energy delivered by the transducer moves radially outwardly with little or no deflection at the balloon and/or the balloon-tissue interface.

Accordingly, the acoustic energy profile of the transducer can be negatively affected by attaching anything to the outside and/or inside surfaces of the transducer tube (e.g., along the outer and/or inner electrodes of the transducer). For example, connecting an electrical conductor of the electrical cable that supplies current to the transducer can results in a diminished or undesirable acoustic energy profile. One embodiment for eliminating the need to attach any electrical conductors or other leads to the outer and inner electrodes of a transducer is illustrated in FIGS. 5 and 6.

In FIGS. 5 and 6, the cylindrical tube 44 can include a distal, non-stepped portion 66 and a proximal, stepped portion 68. As shown, the non-stepped portion comprises an outer electrode 48 along the exterior surface of the tube 44 and an inner electrode 46 along an interior surface of the tube. As discussed in greater detail below, the non-stepped portion of the transducer 16 can comprise a vast majority of the transducer length, such as, for example, 60-90% (e.g., 60-70%, 70-80%, 80-90%, 90-99%, etc.) of the overall length of the transducer 16.

With continued reference to FIGS. 5 and 6, the proximal, stepped portion 68 includes an outer diameter 68a that is less than the outer diameter 66a of the non-stepped portion 66. In other words, the cylindrical tube 44 can comprise a step change in outer diameter along its proximal end. In the depicted embodiments, the stepped portion includes a generally flat or non-sloped step. However, in other embodiments, the step can include, without limitation, a sloped, undulating, roughened or otherwise uneven surface profile. Regardless of its exact shape and configuration, as shown in FIGS. 5 and 6, the stepped portion 68 of the tube can provide a surface on which a conductor of the electrical cable 28 can attach. By placing an additional at least partially electrically conductive material or member along the outside of the conductor at the stepped portion of the tube, the cable can be advantageously electrically coupled to the outer electrode 48 of the transducer without attaching any conductors along an outer diameter or portion of the transducer. Accordingly, the cylindrical outer surface of the transducer can be maintained to provide for a more even acoustic energy profile when the transducer is activated.

In one embodiment, the stepped portion 68 can be fabricated by machining and/or grinding away a proximal portion of the tube's outer diameter 66a. As noted above, such a step can include a uniform or constant outer diameter; however, in other embodiments, the stepped portion comprises a non-flat (e.g., rounded, curved, sloped, etc.) or irregular profile, as desired or required. In other embodiments, the stepped portion 68 can be fabricated by manufacturing the cylindrical tube 44 as a single piece of material with the step integrated into the tube during formation (e.g., by casting or molding the step into the original design). In yet another embodiment, the cylindrical tube 44 with the step can be created as two separate components (e.g., one with a larger diameter and one with the step diameter) which are bonded together (e.g., by welds, adhesives, rivets, screws, threaded couplings or features on the tube itself, press-fit connections, other mechanical or non-mechanical features, etc.).

In one embodiment, the electrical cable 28 that supplies current to the transducer comprises a coaxial cable having an inner conductor 28a and outer tubular conducting shield 28b. As shown in FIG. 6, the inner conductor 28a can be electrically coupled with the outer electrode 48 (e.g., via attachment to the stepped portion), while the outer tubular conducting shield 28b can be electrically coupled with the inner electrode 46 of the cylindrical tube 44. In other embodiments, the conductors of the coaxial cable are reversed and/or different types of electrical cables or connectors can be used.

With continued reference to FIG. 5, one or more rings and/or other components 72 can be placed around the stepped portion 68 of the tube to form a generally constant outer diameter along an entire length of the transducer 16 (e.g., both along the stepped and non-stepped regions). For example, an electrically conductive ring 72 can surround the stepped portion 68 of the cylindrical tube 44 to electrically couple the outer electrode 48 to the inner conductor 28a. The ring 72 can be sized and shaped to have substantially the same outer diameter as the outer diameter 66a of the non-stepped portion 66 and provide a substantially continuous, flat and/or uniform outer surface for the entire transducer. In such an embodiment, the ring 72 can act as an active portion of the transducer 16 and allow for more uniform electrical loading of the ultrasound transducer when the electrical transducer is energized. The ring can be a machined ring having very precise dimensions. The ring, which comprises one or more metals or alloys (e.g., brass, stainless steel, etc.), can include a solid or partially-solid (e.g., having one or more hollow portions or area) design.

In other embodiments, one or more other components can be placed over the stepped portion 68 of the tube. For example, one or more layers of solder or other masses of at least partially electrically conductive can be deposited and secured to the outside of the stepped portion. Such layers or masses can include an outer diameter that matches the outer diameter 66a of the non-stepped portion 66 of the transducer. In some embodiments, an outer surface of the conductive electrical solder or other material or component placed along the outside of the stepped portion is reshaped or otherwise treated to achieve a substantially uniform overall outer diameter for the transducer (e.g., by mechanical grinding, etching, or polishing).

In some embodiments, the stepped portion 68 extends approximately 5% to 25% (e.g., 5% to 10%, 10% to 15%, 15% to 20%, 20% to 25%, etc.) of a length of the cylindrical tube 44. For example, the stepped portion 68 (and the corresponding ring, solder or other material or component placed around the stepped portion) can be approximately 1 mm in length, while the non-stepped portion 66 can be approximately 5 mm in length.

Alternatively, the cylindrical tube 44 can include a stepped portion 68 without an electrically conductive ring or other component 72. In such embodiments, the stepped portion 68 can form an inactive portion of the transducer 16 and the distal, non-stepped portion 66 can form the active portion of the transducer 16. One or more electrical connections (e.g., wires, other conductors, traces, etc.) can be placed along the inactive stepped portion and be routed to the outer electrode of the non-stepped portion 66 of the transducer.

Electrical Impedance Matching

As discussed herein, the ultrasonic transducer 16 can convert input electrical energy into ultrasonic energy that is delivered radially outwardly (e.g., toward target nerve tissue adjacent a vessel wall). In some embodiments, for ultrasonic transducers, the power factor, or conversion rate from electrical energy into generated acoustical energy, can be relatively low. Thus, a large portion of the electrical power delivered by the power supply may be lost as wasted heat. Accordingly, in one embodiment, to increase the efficiency of the ultrasound system, the electrical impedance of the electrical conductors (e.g., the one or more electrical cables 28 that electrically couple the transducer to the power supply) can be matched or substantially matched (e.g., within about 0-10%, 0.1%, 0.2%, 0.3%, 0.4%, 0.5%, 0.5-1%, 1-2%, 2-3%, 3-4%, 4-5%, 5-6%, 6-7%, 7-8%, 8-9%, 9-10%, etc.) to the electrical impedance of the ultrasound transducer 44. Thus, in some embodiments, by matching or substantially matching the impedance values of the cable and the transducer, the electrical load of the system can help reduce or minimize the electrical inefficiency of the system, while increasing or maximizing the amount of power transferred to the transducer.

Accordingly, in some embodiments, the ultrasound system 100 comprises only a single cable (e.g., coaxial cable) routed through a corresponding lumen of the catheter and electrically coupled to the transducer. The electrical cable can be selected to match or substantially match an impedance of the ultrasound transducer. For example, in some embodiments, the impedance of both the electrical cable and the ultrasound transducer is approximately 40 to 60 ohms (e.g., 50, 40-42, 42-44, 44-46, 46-48, 48-50, 50-52, 52-54, 54-56, 56-58, 58-60 ohms, etc.). In other embodiments, the impedance of the electrical cable and the ultrasound transducer can be less than 40 ohms or greater than 60 ohms, as desired or required.

Cooling Fluid Considerations

Figure 7:
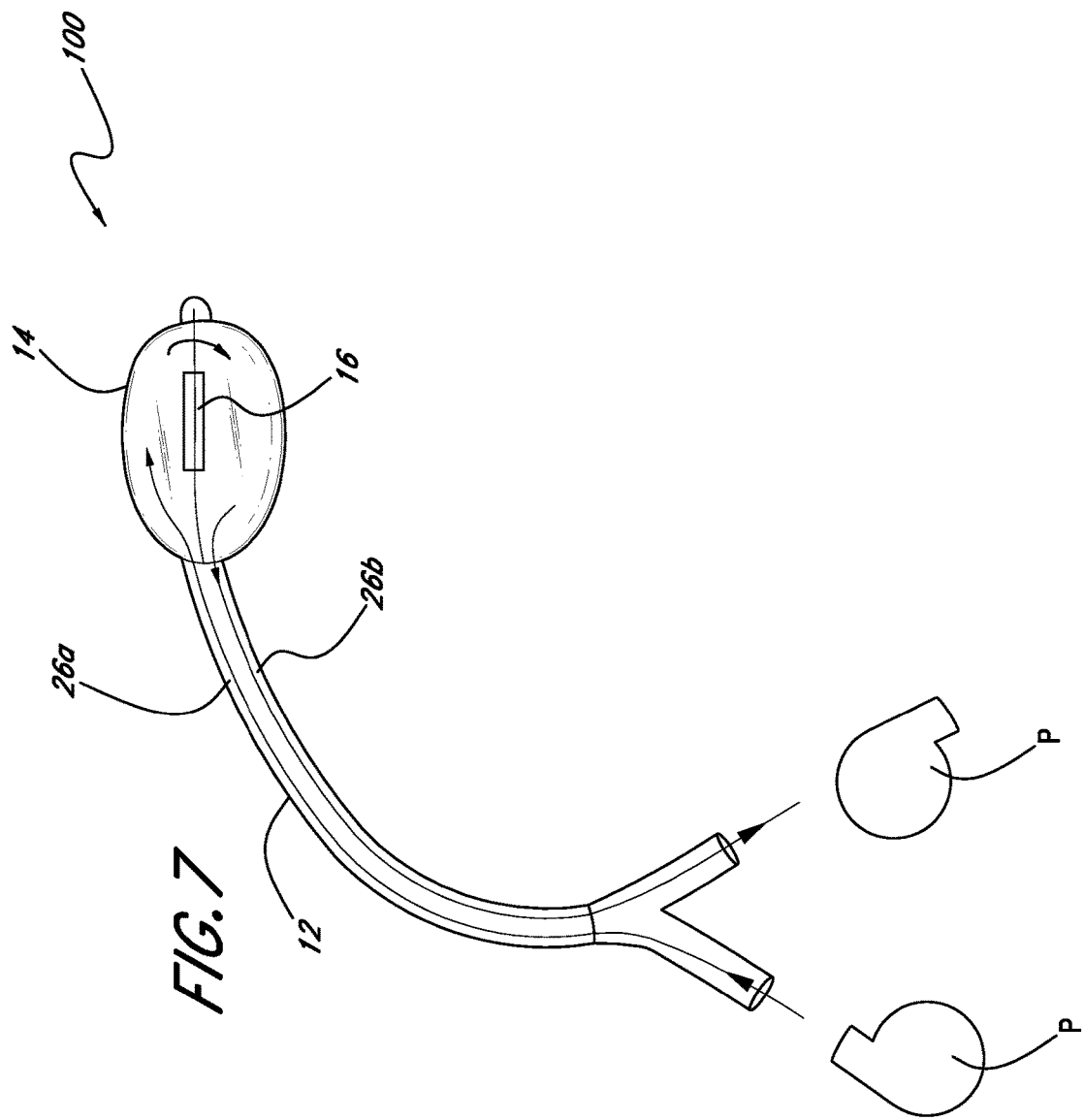
FIG. 7 illustrates the fluid lumens of an ultrasound-based system according to one embodiment.

FIG. 7 schematically illustrates one embodiment of a catheter-based ultrasound system 100 having at least two fluid lumens 26a, 26b positioned within the catheter 12. As shown, each lumen 26a, 26b of the catheter is placed in fluid communication with a separate fluid transfer device (e.g., pump). Further, with reference back to FIG. 1, each lumen 26a, 26b can be in fluid communication with corresponding pumps or other fluid transfer devices (not shown) via ports 34a, 34b (e.g., a luer fittings, other standard or non-standard couplings, etc.). Accordingly, cooling fluid can be injected, infused or otherwise delivered into the vessel to transfer heat away from the transducer and/or other areas at or near the treatment site. As discussed herein, such heat transfer can protect adjacent tissue of the subject (e.g., the wall of the vessel in which the system is placed), can help maintain the transducer within a desired temperature range during use (e.g., for safety and/or performance reasons) and/or the like.

According to some embodiments, the cooling fluid that is circulated through the balloon at the distal end of the system can include, for example, saline, water or any other liquid or fluid. The cooling fluid can be room temperature or actively cooled (e.g., relative to room temperature, body temperature, etc.), as desired or required. In some embodiments, cooling fluid is circulated through the system in such a manner so that a the temperature along the interior wall of the vessel surrounding the transducer is maintained at a temperature of about 50-55° C. (e.g., 50° C., 51° C., 52° C., 53° C., 54° C., 55° C., etc.). In addition, in some embodiments, the temperature of the vessel wall is maintained within such a target range (e.g., 50-55° C.), while the temperature of tissue approximately 0.5 mm to 8 mm (e.g., 1 mm to 6 mm, where, in some embodiments, target tissue is located) is heated to about 60-80° C. (e.g., 60-70° C., 70-80° C., 65-75° C., etc.) when the transducer is activated. The higher temperature at a particular distance away from the vessel wall can be due, at least in part, on the less effective cooling by the cooling fluid at those distances away from the balloon. In some embodiments, raising the temperature of nerve and/or other nerve tissue to about 60-80° C. can help perform the desired neuromodulation (e.g., ablation, necrosing, etc.) to such tissue. A treatment protocol that accomplishes the desired heating of the targeted tissue (e.g. nerves) while maintaining adjacent vessel tissue to safe levels (e.g., to reduce the likelihood of stenosis or other damage to such tissue) can be based, either completely or in part, on empirical or experimental data.

Certain vessels (e.g., renal arteries) in which the system can be placed can have a relatively small catheter diameter. As a result, the diameter of the fluid lumens 26a, 26b located within the catheter may also need to be reduced. As the diameter of the fluid lumens 26 are decreased, the pressure required to move the cooling fluid increases (e.g., due to an increase in back pressure and head losses through the fluid lumens). As a result, increased cooling fluid pressure can be required by one or more of the pumps or other fluid transfer devices in fluid communication with the system. However, if the system fluid pressure is increased to a high enough value, the increased pressure of the balloon can create one or more safety concerns. For example, the balloon itself may be susceptible to rupture or other damage. Further, the pressure created within the balloon can cause the balloon to expand to a degree that poses a risk of harm to the adjacent tissue of the subject (e.g., the artery or other vessel of the subject may rupture or otherwise be damaged). Accordingly, in some embodiments, it is desirable to regulate and limit the pressure within the balloon. For example, in some embodiments, the internal pressure of the balloon 14 is maintained at about 1.5-2 ATM (e.g., for a 6 FR catheter).

As illustrated in FIG. 7, in one embodiment, the fluid lumens 26a, 26b can include a delivery lumen 26a and a return lumen 26b for supplying and returning cooling fluid to and from, respectively, the balloon or other expandable member 14. The use of separate fluid lumens 26a, 26b can help reduce the overall internal pressure of the balloon during use, while still being able to circulate cooling fluid at a target flowrate through the balloon interior. Thus, a desired flowrate of cooling fluid can be sustained through the system without over-pressurizing the balloon 14. This is due, in part, because the vacuum created through the return lumen 26b (e.g., by one of other pumps P) helps reduce the pressure within the balloon interior accordingly. By way of example, the delivery lumen 26a can have a pressure of approximately 70 psig and the return lumen 26b can have a vacuum of 10 psig. Thus, under those circumstances, the internal pressure of the balloon is about 30 psig (e.g., (70 psig-10 psig)/2)=30 psig).

In one embodiment, the pumps P or other fluid transfer devices that are placed in fluid communication with the fluid lumens 26a, 26b comprise positive displacement pump, such as a peristaltic pump. However, in some circumstances, when the back-pressures associated with delivering the cooling fluid to the balloon is above a particular threshold, peristaltic pumps or similar positive displacement pumps are unable to deliver the necessary flowrate of cooling fluid to the balloon.

Accordingly, in some embodiments, one or more pumps P of the systems can comprise a syringe pump. A syringe pump can include a reservoir for storing a volume of cooling fluid and a movable member configured to move (e.g., slide) within an interior of the reservoir. The movement of the movable member within the corresponding reservoir exerts the necessary backpressure on the fluid (e.g., cooling fluid) stored within the reservoir and transfers the fluid through the fluid delivery lumen 26a of the catheter and into the balloon. In some embodiments, the use of such syringe pumps can provide sufficient force to achieve the required backpressure at a desired flowrate of cooling fluid. The movable members of syringe or other such pumps can be selectively moved by one or more stepper motors or other mechanical devices. In such embodiments, the stepper motor can prevent and/or minimize deflection of the movable member caused by the corresponding torques, moments and forces.

According to some embodiments, the reservoir of the syringe or other pump P in fluid communication with the fluid lumen 26a and the balloon 14 is sized and otherwise configured to store a sufficient volume of cooling fluid for an entire treatment procedure. In some embodiments, the volume of the reservoir is approximately 50 ml to 1,000 ml (e.g., 50-100, 100-200, 200-300, 300-400, 400-500, 500-600, 600-700, 700-800, 800-900, 900-1,000 ml, capacities between the foregoing, etc.).

In one embodiment, the fluid lumens 26 can be operated simultaneously to circulate cooling fluid through the expandable members 14 during an ablation procedure. In one embodiment, the flowrate of cooling fluid through the lumens 26 can be between 30-50 ml/min (e.g., 30-40 ml/min, 40-50 ml/min, 35-45 ml/min, 40 ml/min).

IV Bag Connector

Figure 8:
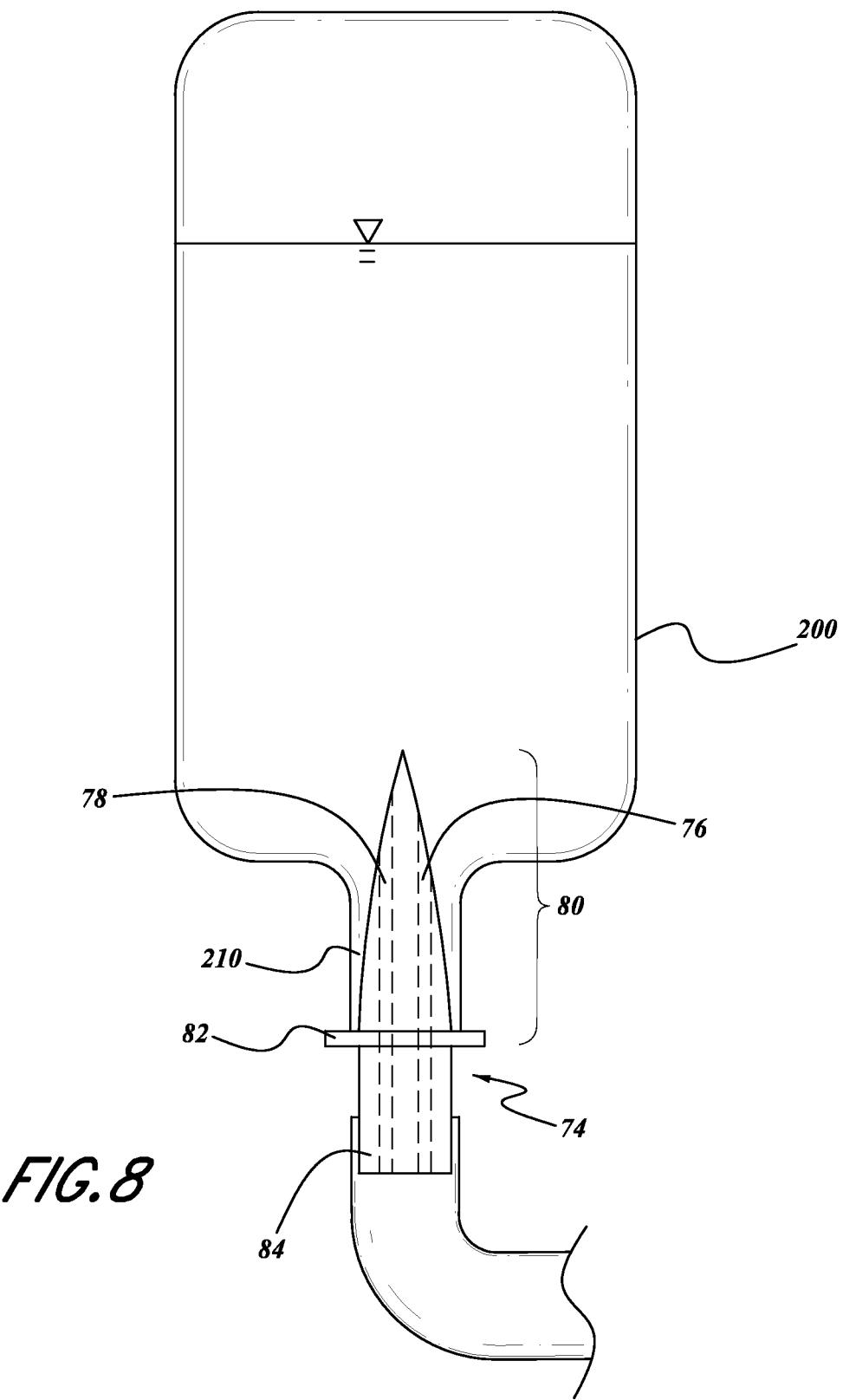
FIG. 8 illustrates an IV bag and spike or coupling inserted therein according to one embodiment.

IV bags used for the storage of cooling fluid in connection with the various systems disclosed herein can have two outlet ports (e.g., for mating to the two fluid lumens 26 of the catheter). In other embodiments, however, the IV bag 200 is constructed with only a single inlet/outlet port 210, as depicted in FIG. 8. In such embodiments, a dual lumen spike or coupling 74 can be inserted within the port 210 of the IV bag 200 to enable fluid to be transferred both to and from the bag. This can effectively turn a single-port IV bag into a dual port IV bag without redesigning the bag itself.

In some embodiments, the dual lumen spike or coupling 74 can comprise two or more lumens or passages 76, 78 that are separated from one another. Such separate passage 76, 78 can be connected to different fluid conduit or sources, as desired or required. As shown, the spike 74 can include a proximal hub 82 that is shaped, sized and otherwise configured to abut against an end of bag's port 210 (or other inlet or outlet). A proximal conduit 84 can be inserted within or otherwise placed in fluid communication with one or more fluid sources (e.g., lumen of a catheter as disclosed herein, a pump, etc.). In some embodiments, the spike can include a minimum penetration depth 80 into the IV bag to ensure adequate flow (e.g., supply and return) into and out of the bag. Such a minimum penetration depth can help prevent or reduce the likelihood of short-circuiting of fluids entering and exiting the bag 200. In some embodiments, the inner diameters of the internal lumens or passages 76, 78 of the spike or coupling 74 are approximately 0.05 to 0.125 inches (e.g., 0.05-0.06, 0.06-0.07, 0.07-0.08, 0.08-0.09, 0.09-0.1, 0.1-0.11, 0.11-0.125, diameter between the foregoing, etc.) and the minimum penetration distance 80 is about 1.5 inches (e.g., 0.75, 1.0, 1.25, 1.5 inches, distances between the foregoing, less than 0.75 inches, more than 1.5 inches, 1.5-2.0 inches, 2.0-3.0 inches, more than about 3 inches, etc.).

In some embodiments, such a coupling or spike 74 can be used on an IV bag or other fluid container that is placed in fluid communication with a syringe pump of a treatment system. Thus, the IV bag can be configured to store additional fluid that will be delivered through a delivery lumen into a balloon and/or can be configured to store excess fluid being returned from the balloon via a return lumen in the catheter. Thus, the coupling 74 can be placed in fluid communication with the catheter and/or the syringe pump of the treatment system.

Vessel Diameter Detection

In some embodiments, prior to inflation of a balloon or other expandable member 14, the ultrasonic transducer 16 can be activated to measure the vessel's diameter. This can be accomplished by sending out a single (or a distinct number of) ultrasonic waves and recording the time period required for the signals to return (e.g., bounce back) to the transducer surface. Thus, in some embodiments, a control system of the system can be configured to both emit acoustic energy and detect it (e.g., at or along the outside of the transducer). By detecting the diameter of the vessel (e.g., renal artery) at a desired treatment location, the clinician can make any necessary adjustments to the procedure (e.g., what size balloon to use, how much energy should be delivered to the subject and for what time period, etc.).

Miscellaneous Concepts

In any of the embodiments disclosed herein, the system can comprise an ultrasound transducer having a variety of shapes. The transducer can be cylindrical or non-cylindrical, as desired or required. For example, in some embodiments, the transducer comprises, at least in part, an hourglass shape, a barbell shape, a convex shape or surface, a concave shape or surface and cone shape, an irregular shape and/or the like.

In some embodiments, a system can comprise an array of transducers (e.g., an array comprising 2, 3, 4, 5, 6, 7, 8, 9, 10, 10-15, more than 15 transducers, etc.). In embodiments comprising 2 or more transducers (e.g., an array of transducers), one or more of the transducers can be configured to emit more or less ultrasonic energy than one or more other transducers. In some embodiments, the amount of acoustic energy that is emitted by the plurality of transducers varies (e.g., linearly, non-linearly, randomly, etc.) along a longitudinal axis of the system. In some embodiments, one or some ultrasound transducer of a system emit (or are configured to emit) greater acoustic energy in one or more directions in relation to one or more other directions.

In any of the embodiments disclosed herein, an ultrasound transducer can include differing wall thickness (e.g., along its longitudinal axis). In embodiments comprising two or more transducers, the wall thickness of one transducer is greater or less than the wall thickness of another transducer. In some embodiments, one or more transducers of a system can be independently controllable (e.g., such that power and/or frequency to one transducer can be different than power and/or frequency to another transducer, etc.). In some embodiments, two or more transducers of a system are controlled together or in unison. In one embodiment, a transducer can include an eccentric or non-uniform backing lumen or opening.

In any of the embodiments disclosed herein, the transducer comprises a varying wall thickness along at least a portion of its circumferential extent. Accordingly, rotating the transducer can alter the acoustic energy pattern emitted by the transducer and/or alter one or more other aspects of energy emission (e.g., frequency, efficiency, etc.) during use. In some embodiments, one or more regions, surfaces and/or other portions of a transducer can be at least partially masked, covered, obstructed, etc. in order to alter the acoustic energy profile of the transducer during use. For example, at least a portion of the transducer can be masked or otherwise covered by selective plating and/or etching of the electrodes along the transducer, covering a portion of the transducer, using one or more features of the balloon, etc.).

In some embodiments, ultrasonic energy is directed directly within the tissue of the targeted nerve tissue (e.g., sympathetic nerves). In any of the embodiments disclosed herein, a balloon and/or other expandable structure or member can be used to at least partially expand the area or volume of tissue being treated (e.g., the renal artery, other body lumen or vessel, etc. can be radially expanded). In some embodiments, an ablation system includes a balloon (e.g., positioned at least partially around one or more transducers), but no fluid is configured to be circulated through the balloon during use. For example, in one embodiment, the balloon can be inflated with one or more gases, liquids and/or fluids (e.g., in order to expand the balloon, so that balloon contacts the adjacent wall of the targeted vessel, so that the one or more transducers of the system are radially centered or generally radially centered within the vessel, etc.), but no fluids are circulated through the balloon. Thus, the balloon can be configured to maintain an inflated or expanded state without the continuous or intermittent delivery of fluid therethrough.

In some embodiments, a catheter of the system comprises a chip (e.g., a smart catheter) and/or one or more related components or features (e.g., an identification device or reader, a transducer, etc.). Accordingly, the generator can detect which catheter is being used. Further, the system can monitor one or more aspects of a therapy or procedure using one or more metrics that are detected, such as, for example, pressure, temperature, flowrate, vessel diameter, thermal profile, presence and/or degree of spasm of a vessel, degree of narrowing of a vessel and/or the like. Such information can be used in a control scheme to regulate one or more aspect of the generator and/or other components or devices of the system (e.g., to modulate power, frequency, duration of procedure, automatic shutoff, billing, patient records or other recordkeeping, memorization of a procedure for other reasons, etc.).

The features and attributes of the specific embodiments disclosed herein may be combined in different ways to form additional embodiments, all of which fall within the scope of the present disclosure. Although the concepts presented herein have been disclosed in the context of certain embodiments and examples, the present application extends beyond the specifically disclosed embodiments to other alternative embodiments and/or uses of the concepts disclosed herein and obvious modifications and equivalents thereof. The disclosure herein of any particular feature, aspect, method, property, characteristic, quality, attribute, element, or the like in connection with an embodiment can be used in all other embodiments set forth herein. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." For all of the embodiments described herein the steps of the methods need not be performed sequentially. Thus, it is intended that the scope of the concepts disclosed herein should not be limited by the particular disclosed embodiments described above.

What is claimed is:

1. An intravascular, ultrasound-based ablation system comprising:
   a catheter comprising a guidewire lumen, at least one cable lumen and at least one fluid lumen;
   a balloon positioned at a distal end of the catheter, an interior of the balloon being in fluid communication with the at least one fluid lumen of the catheter, wherein the balloon is configured to inflate when fluid is delivered into the interior through the at least one fluid lumen of the catheter;
   a tip extending distally from a distal end of the balloon, the tip comprising an internal guidewire passage;
   an ultrasound transducer positioned within the balloon, the ultrasound transducer comprising a cylindrical tube having proximal and distal ends, an outer surface and a lumen defining an inner surface, an inner electrode disposed on the inner surface and an outer electrode disposed on the outer surface;
   at least one electrical cable positioned within the at least one cable lumen of the catheter, the at least one electrical cable comprising a first connector and a second connector, the first connector being electrically coupled to the outer electrode and physically attached to a portion of the outer surface of the ultrasound transducer not having the outer electrode, and the second connector being electrically coupled to the inner electrode; and
   a transducer support structure consisting of:
      a backing member disposed within the lumen and inner electrode, the backing member extending from the proximal end to the distal end of the cylindrical tube and defining an interior lumen;
      an electrically insulating material disposed along the interior lumen of the backing member; and
      a plurality of attachment points extending from the backing member, the plurality of attachment points configured to engage the inner electrode, spacings between the plurality of attachment points defining a plurality of openings;
   wherein the plurality of attachment points define an internal space between the backing member and the inner electrode, the internal space being in fluid communication with the interior of the balloon via the plurality of openings so that, when in use, fluid entering the balloon passes along the outer electrode and into the internal space between the backing member and the inner electrode through the plurality of openings to transfer heat away from the ultrasound transducer, the backing member is generally aligned with the guidewire lumen of the catheter and the internal guidewire passage of the tip to permit the system to be delivered to a desired vascular position over a guidewire, and the backing member serves as a fluid barrier between fluid circulated within the balloon interior and the interior lumen.

2. The system of claim 1,
   wherein the electrically insulating material comprises polyimide; and
   wherein the guidewire lumen extends from a proximal end of the catheter to the balloon.

3. The system of claim 1, wherein the electrically insulating material prevents electrical conduction between a guidewire and the backing member.

4. The system of claim 3, wherein the electrically insulating material comprises polyimide.

5. The system of claim 1, wherein the guidewire lumen extends from a proximal end of the catheter to the balloon.

6. The system of claim 1, wherein the guidewire lumen extends from a location between the proximal and distal ends of the catheter to the distal end of the catheter, such that the catheter comprises a rapid exchange design.

7. The system of claim 1, wherein the backing member and plurality of attachment points are integrally formed.

8. An intravascular, ultrasound-based ablation system comprising:
   a catheter comprising at least one cable lumen and at least one fluid lumen;
   a balloon positioned at a distal end of the catheter, an interior of the balloon being in fluid communication with the at least one fluid lumen of the catheter;
   a tip extending distally from a distal end of the balloon, the tip comprising an internal guidewire passage;
   an ultrasound transducer positioned within the balloon, the ultrasound transducer comprising a cylindrical tube having a proximal end and a distal end, an inner surface, an outer surface, an inner electrode disposed on the inner surface and an outer electrode disposed on the outer surface; the proximal end of the cylindrical tube comprising a stepped portion, wherein a portion of an outer diameter of the cylindrical tube is smaller than a portion of the outer diameter of the cylindrical tube located distal to the stepped portion such that the outer electrode is not disposed on the stepped portion;

at least one electrical cable positioned within the at least one cable lumen of the catheter, the at least one electrical cable comprising a first connector and a second connector, the first connector being electrically coupled to the outer electrode and physically attached to a portion of the outer surface of the ultrasound transducer not having the outer electrode, and the second connector being electrically coupled to the inner electrode;

a transducer support structure disposed within the lumen of the cylindrical tube, the transducer support structure having a plurality of attachment points configured to engage the inner electrode, the plurality of attachment points defining a plurality of openings; and a backing member coupled to the transducer support structure and disposed within the lumen and the inner electrode, the transducer support structure defining an internal space between the backing member and the inner electrode, the internal space being in fluid communication with the interior of the balloon via the plurality of openings so that, when in use, fluid entering the balloon passes along the outer electrode and into the internal space between the backing member and the inner electrode through the plurality of openings to transfer heat away from the ultrasound transducer, the backing member further comprising an interior lumen that is generally aligned with the guidewire lumen of the catheter and the internal guidewire passage of the tip to permit the system to be delivered to a desired vascular position over a guidewire, wherein the backing member is electrically coupled to the second connector.

9. The system of claim 8, further comprising a ring surrounding the stepped portion, the ring being sized and shaped to surround the portion of the outer diameter of the cylindrical tube located distal to the stepped portion, the ring being electrically conductive so that the first connector is electrically coupled to the electrode along the outer surface of the cylindrical tube;
wherein the ring comprises a conductive machined ring that couples around the stepped portion of the cylindrical tube; and
wherein the stepped portion extends approximately 5% to 25% of a length of the cylindrical tube.

10. The system of claim 9, wherein the ring comprises conductive solder.

11. The system of claim 9, wherein the ring comprises a conductive machined ring that couples around the stepped portion of the cylindrical tube.

12. The system of claim 8, wherein the stepped portion extends approximately 5% to 25% of a length of the cylindrical tube.

13. The system of claim 8, wherein the stepped portion comprises a portion of the cylindrical tube that is removed using grinding or other removal techniques.

14. The system of claim 8, wherein an impedance of the at least one electrical cable substantially matches an impedance of the ultrasound transducer.

15. The system of claim 14, wherein the impedance of the electrical cable and the ultrasound transducer is approximately 40 to 60 ohms.

16. The system of claim 8, wherein the backing member and transducer support structure are integrally formed.

17. An intravascular, ultrasound-based ablation system comprising:
a catheter comprising a cable lumen extending from a proximal end to a distal end of the catheter;
a balloon positioned at a distal end of the catheter;
a tip extending distally from a distal end of the balloon;
an ultrasound transducer positioned at or near a distal end of the catheter, the ultrasound transducer comprising a cylindrical tube having an inner surface and an outer surface, and an inner electrode disposed on the inner surface and an outer electrode disposed on the outer surface, a proximal portion of the cylindrical tube having a stepped portion such that the outer electrode is not disposed on the stepped portion;
a transducer support structure having a plurality of attachment points configured to engage the inner electrode, spacings between the plurality of attachment points defining a plurality of openings, the transducer support structure being electrically coupled to the inner electrode;
a backing member extending through the cylindrical tube, the transducer support structure defining an internal space between the backing member and the inner electrode, the internal space being in fluid communication with an interior of the balloon via the plurality of openings so that, when in use, fluid entering the balloon passes along the outer electrode and into the internal space between the backing member and the inner electrode through the plurality of openings; and
an electrical cable positioned within the cable lumen of the catheter and extending from the proximal end to the distal end of the catheter, wherein a proximal end of the electrical cable is configured to be coupled to a generator configured to selectively provide electrical power to the ultrasound transducer through the electrical cable, the electrical cable comprising a first connector and a second connector, the first connector being electrically coupled to the outer electrode and physically attached to a portion of the outer surface of the ultrasound transducer not having the outer electrode, and the second connector being electrically coupled to the backing member;
wherein an impedance of the electrical cable is substantially equal to an impedance of the ultrasound transducer, thereby providing a more efficient power transfer from the generator to the ultrasound transducer when the ablation system is in use.

18. The system of claim 17,
wherein the electrical cable comprises a coaxial cable; and
wherein the impedance of the electrical cable and the ultrasound transducer is approximately 40 to 60 ohms.

19. The system of claim 17, wherein the electrical cable comprises a coaxial cable.

20. The system of claim 17, wherein the impedance of the electrical cable and the ultrasound transducer is approximately 40 to 60 ohms.

21. The system of claim 17, wherein the backing member and transducer support structure are integrally formed.

* * * * *